United States Patent
Tanaka

(10) Patent No.: US 10,188,300 B2
(45) Date of Patent: Jan. 29, 2019

(54) INFRARED THERMOMETER

(71) Applicant: BIO ECHO NET INC., Sapporo-shi, Hokkaido (JP)

(72) Inventor: Hideki Tanaka, Hokkaido (JP)

(73) Assignee: BIO ECHO NET INC., Sapporo-Shi, Hokkaido (JP)

( * ) Notice: Subject to any disclaimer, the term of this patent is extended or adjusted under 35 U.S.C. 154(b) by 396 days.

(21) Appl. No.: 15/011,994

(22) Filed: Feb. 1, 2016

(65) Prior Publication Data
US 2016/0157732 A1   Jun. 9, 2016

Related U.S. Application Data

(63) Continuation of application No. PCT/JP2014/069746, filed on Jul. 25, 2014.

(30) Foreign Application Priority Data

Aug. 7, 2013  (JP) .................................. 2013-164082
Feb. 5, 2014  (JP) .................................. 2014-020017

(51) Int. Cl.
*A61B 5/01*    (2006.01)
*G01J 5/08*    (2006.01)
(Continued)

(52) U.S. Cl.
CPC ................ *A61B 5/01* (2013.01); *A61B 5/742* (2013.01); *G01D 5/24* (2013.01); *G01J 5/0025* (2013.01);
(Continued)

(58) Field of Classification Search
None
See application file for complete search history.

(56) References Cited

U.S. PATENT DOCUMENTS 5,424,717 A * 6/1995 Platt ..................... G01S 7/491
                                             340/557
6,382,790 B1 * 5/2002 Girod .................. B24B 13/0012
                                             351/159.74
(Continued)

FOREIGN PATENT DOCUMENTS

JP    2005-342376    12/2005
JP    2006-110363     4/2006
(Continued)

OTHER PUBLICATIONS

Lai, "Kilohertz scanning optical delay line employing a prism array", Applied Optics, 2001, vol. 40, No. 34, pp. 6334-6336.*
(Continued)

*Primary Examiner* — Katherine Fernandez
*Assistant Examiner* — Yi-Shan Yang
(74) *Attorney, Agent, or Firm* — Procopio, Cory, Hargreaves & Savitch LLP

(57) ABSTRACT

An infrared thermometer for measuring a body temperature in no contact with a human body includes: a main unit incorporating an infrared sensor; a distance sensor detecting a distance between the main unit and the human body when the main unit approaches the human body; and a controller for calculating the body temperature based on quantity of infrared from the infrared sensor when the distance sensor detects that the distance between the main unit and the human body is within a predetermined distance. The distance sensor includes: a light source; a projector lens for projecting light of the light source toward the human body; a light receiving sensor; and a light receiving lens that allows the light receiving sensor to receive return light of the light, which is obtained as a result of being reflected by the human body, when the main unit is located within the predetermined distance.

6 Claims, 21 Drawing Sheets

(51) Int. Cl.
  *G01J 5/02* (2006.01)
  *G01J 5/04* (2006.01)
  *G01J 5/14* (2006.01)
  *G01J 5/00* (2006.01)
  *A61B 5/00* (2006.01)
  *G01D 5/24* (2006.01)

(52) U.S. Cl.
  CPC ............ *G01J 5/026* (2013.01); *G01J 5/0265* (2013.01); *G01J 5/0275* (2013.01); *G01J 5/04* (2013.01); *G01J 5/0875* (2013.01); *G01J 5/14* (2013.01)

(56) References Cited

U.S. PATENT DOCUMENTS

| | | | |
|---|---|---|---|
| 6,527,439 | B1 | 3/2003 | Bellifemine |
| 7,022,962 | B2 * | 4/2006 | Ohtomo ............... G01C 15/004 250/206.1 |
| 2003/0099277 | A1 * | 5/2003 | Bellifemine .......... G01J 5/0022 374/121 |
| 2008/0246625 | A1 | 10/2008 | Chen et al. |
| 2008/0317403 | A1 * | 12/2008 | Kubo .................... G02B 6/264 385/14 |
| 2011/0085433 | A1 * | 4/2011 | Takada .................... G02B 3/04 369/112.23 |
| 2011/0106484 | A1 | 5/2011 | Quinn et al. |
| 2013/0241761 | A1 * | 9/2013 | Cooper ................ G01S 7/4812 342/54 |

FOREIGN PATENT DOCUMENTS

| | | |
|---|---|---|
| JP | 2012-217563 | 11/2012 |
| JP | 2012217563 A | 11/2012 |
| KR | 101138955 B1 | 4/2012 |

OTHER PUBLICATIONS

Extended European Search Report for PCT/JP2014/069746 dated Aug. 31, 2017, 11 pages.
International Search Report for PCT App No. PCT/JP2014/069746 dated Oct. 28, 2014, 8 pgs.
Partial Supplementary European Search Report for EP App No. 14834841.0 dated May 17, 2017, 11 pgs.

* cited by examiner

INFRARED THERMOMETER

CROSS REFERENCE TO RELATED APPLICATIONS

This application is a continuation of International Application No. PCT/JP2014/069746, filed Jul. 25, 2014, and based upon and claims the benefit of priority from Japanese Patent Applications No. 2013-164082, filed Aug. 7, 2013, and No. 2014-020017, filed Feb. 5, 2014, the entire contents of all of which are incorporated herein by reference.

BACK GROUND

Technical Field

The present application relates to an infrared thermometer using an infrared sensor to measure a body temperature contactlessly.

Related Art

Because an infrared thermometer using an infrared sensor for measuring a body temperature is capable of measuring the body temperature quickly, the infrared thermometer is extremely effective for measurement of the body temperature of a subject, such as a baby or an infant, who tends to cry easily, sleep or move constantly.

The infrared sensor is adapted so as to measure the quantity of infrared radiated from a measuring object portion, such as a human skin, thereby measuring a temperature of the measuring object portion, that is, the body temperature. However, as the infrared attenuates in inverse proportion to the square of the distance, it is required to precisely measure a distance between the infrared sensor and the measuring object portion or make the distance up to the measuring object portion constant, for measurement of the quantity of infrared.

In a conventional infrared thermometer, therefore, since the setting or measurement of the distance between the infrared sensor and the measuring object portion has been performed by a measurer's action of "adjusting the distance to about several cm", "aligning with an optical mark" or the like, the setting or measurement did depend on a measurer's skill largely. For this reason, it was difficult to measure a precise body temperature heretofore since measurement error occurred in the distance between the infrared and the measuring object portion frequently.

An infrared thermometer for solving the problem of such a distance error is disclosed in PTL 1 (JP 2012-217563 A). In the infrared thermometer disclosed in PTL 1, a main unit having a built-in infrared sensor is adapted so as to measure the quantity of infrared from the infrared sensor when contact-judgment means judges that the thermometer has directly touched a human skin, e.g. a baby's skin, and calculate the body temperature based on the so-measured quantity of infrared.

SUMMARY

However, as the infrared thermometer described in PTL 1 is constructed so as to touch the skin of a human body, for example a baby's skin, directly, transfer of the body temperature from the baby to a casing of the infrared thermometer could produce an error in the measurement of the body temperature.

Under the above-mentioned situation, an object of the present application is to provide an infrared thermometer capable of measuring a precise body temperature because there is no transfer of the body temperature in measuring the body temperature contactlessly since the infrared thermometer, despite its simple structure, does not touch the skin of a human body as a subject being inspected, for example, a baby.

To achieve the above object, an infrared thermometer according to a first aspect of the present application is an infrared thermometer capable of measuring a body temperature in no contact with a human body, including: a main unit incorporating an infrared sensor; a proximity sensor configured to detect that the main unit has been positioned in proximity to the human body; and a controller configured to calculate the body temperature of the human body based on quantity of infrared from the infrared sensor when the proximity sensor has detected a positioning of the main unit in proximity to the human body, wherein the proximity sensor includes a ground electrode and a plurality of segmented electrodes arranged around the ground electrode, and the controller is configured to measure electrostatic capacitances between the ground electrode and the segmented electrodes respectively and measure a distance between the main unit and the human body based on the electrostatic capacitances, thereby detecting a tilt angle of the main unit with respect to the human body.

With this configuration, it is possible to detect the tilt angle of the main body to the human body. Thus, as the infrared thermometer does not touch a skin of the human body as a subject being inspected, for example, a baby, there is no transfer in body temperature during the contactless body-temperature measurement, so that an accurate body temperature can be measured by precisely orientating the posture of the main unit to the human body.

The controller may have a reference table for correcting the measured body temperature and correct the body temperature that has been already measure by referring to the reference table from the detected tilt angle.

With this configuration, the controller refers to the reference table. Thus, even though the main unit is inclined to the human body, the measured body temperature can be corrected in response to the tilt angle, and thus it is possible to measure the body temperature more accurately.

The ground electrode may be formed into a ring shape, while the plurality of segmented electrodes may be formed by dividing a ring-shaped electrode outside the ground electrode.

With this configuration, the electrostatic-capacity type proximity sensor is structured to have the grounding electrode and the multiple divided electrodes. Thus, such a structure has a degree of freedom for design and therefore, it is easy to incorporate the proximity sensor into the infrared thermometer.

The infrared thermometer may include a notification unit that notifies, when the tilt angle of the main unit to the human body exceeds a predetermined tilt angle, that effect and that also notifies, when measurement of the body temperature is finished, a completion of the measurement.

With this configuration, a measurer can know that the main unit is not being directed to the human body in a correct posture but being inclined to the human body, through the notification unit. Furthermore, the measurer can know that the measurement of the body temperature is finished, by a notification from the notification unit.

An infrared thermometer according to a second aspect of the present application is an infrared thermometer capable of measuring a body temperature in no contact with a human body, including: a main unit incorporating an infrared sensor, a distance sensor configured to detect a distance between the main unit and the human body when the main unit approaches the human body; and a controller configured to calculate the body temperature of the human body based on quantity of infrared from the infrared sensor when the distance sensor detects that the distance between the main unit and the human body has become a predetermined distance, wherein the distance sensor includes: a light source for emitting light; a projector lens for projecting the light of the light source toward the human body; a light receiving sensor; and a light receiving lens that allows the light receiving sensor to receive return light of the light, which is obtained as a result of being reflected by the human body, when the main unit is located at the predetermined distance.

With this configuration, when the main unit is located at the predetermined distance, it is carried out to allow the light receiving sensor to receive the return light of the projected light, which is obtained as a result of being reflected by the human body, and further calculate the body temperature of the human body at the predetermined distance based on the quantity of infrared from the infrared sensor. Thus, as the infrared thermometer, despite its simple structure, does not touch a skin of the human body as a subject being inspected, for example, a baby, there is no transfer in body temperature during the contactless body-temperature measurement, thereby allowing the body temperature to be measured precisely.

Both the projector lens and the light receiving lens may be semi-circular arc-shaped lenses in common.

By adopting semi-circular arc-shaped lenses for the projector lens and the light receiving lens in common, the infrared sensor can be disposed between the projector lens and the light receiving lens. Therefore, the layout of the infrared sensor in the main unit is easy and accordingly, miniaturization of the main unit can be carried out.

The infrared thermometer may include a circuit board on which the projector lens, the light receiving lens and the infrared sensor are mounted. Further, the infrared sensor may be arranged between the projector lens and the light receiving lens, while the projector lens and the light receiving lens may be arranged at symmetrical positions with respect to a center axis passing through the infrared sensor, as a center.

With this configuration, the infrared sensor can receive infrared radiation from the human body through an interval between the projector lens and the light receiving lens.

The circuit board, which mounts the infrared sensor, the light receiving lens and the projector lens thereon, may be arranged in an apex portion of the main unit.

With this arrangement, the body temperature can be measured by moving the apex portion of the main unit closer to the human body.

Both a tip of the projector lens for projecting the light and a tip of the light receiving lens for receiving the return light may be inclined at a constant angle so as to have a single focal length.

With this configuration, it is possible to receive the return light on the side of the light receiving lens with the single focal length determined by the angle of the tip.

Both a tip of the projector lens for projecting the light and a tip of the light receiving lens for receiving the return light change continuously so as to have a plurality of different focal lengths.

With this configuration, it is possible to receive the return light on the side of the light receiving lens with the multiple focal lengths determined by the angle of the tip.

Both a tip of the projector lens for projecting the light and a tip of the light receiving lens for receiving the return light change in a stepwise shape so as to have a plurality of different focal lengths at respective positions from each center to respective ends.

With this configuration, it is possible to receive the return light on the side of the light receiving lens with the multiple focal lengths determined by the angle of the tip.

With the aspects of the present application, it is possible to provide an infrared thermometer capable of measuring a precise body temperature because there is no transfer of the body temperature in measuring the body temperature contactlessly since the infrared thermometer, despite its simple structure, does not touch a skin of a human body as a subject being inspected, for example, a baby.

DETAILED DESCRIPTION

Embodiments will be described with reference to accompanying drawings.

First Embodiment

An infrared thermometer 1 according to a first embodiment will be described with reference to FIGS. 1 to 12.

Figure 1:
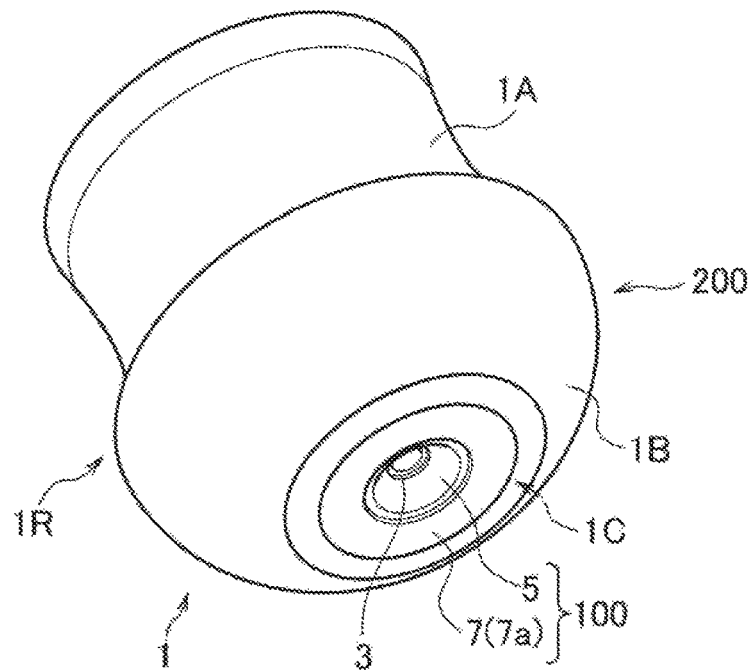
FIG. 1 is a perspective view of an infrared thermometer according to a first embodiment.

As illustrated in FIG. 1, the infrared thermometer 1 according to the first embodiment includes a cover 200. The cover 200 is configured so as to be slightly-vertical barrel-shaped. Owing to this configuration, it is easy for a measurer to pinch a concave portion 1A etc. which is slightly recessed at the center of the cover 200, by fingers. Then, the measurer is supposed to pinch the concave portion 1A of the cover 200 of the infrared thermometer 1 and also measure a body temperature in no contact, at a position closer to a measuring target whose body temperature is to be measured, for example, a human skin positioned at the central part of a forehead of a human body, such as a baby's body.

Consequently, the infrared thermometer 1 is in no contact with the human skin. In other words, as the infrared thermometer does not touch a skin of a human body (e.g. baby) as a subject being inspected, there is no possibility that heat (body temperature) is transferred from the skin to the infrared thermometer 1, so that it is possible to measure more accurate body temperature.

As illustrated in FIG. 1, the infrared thermometer 1 includes an infrared sensor 3 for measuring a body temperature and a proximity sensor 100 for measuring a distance between a measuring object portion of a human body, and an apex portion 1B of the infrared thermometer 1. In the infrared thermometer 1, a substantially central portion of the front side of a main unit 1R, that is, a substantially central portion of the apex portion 1B of the cover 200, which is directed downward to the right as illustrated in FIG. 1, is recessed in a mortar shape to constitute a mortar-shaped portion 1C. The infrared sensor 3 and the proximity sensor 100 are attached to a recessed portion at the center of the mortar-shaped portion 1C.

Figure 2:
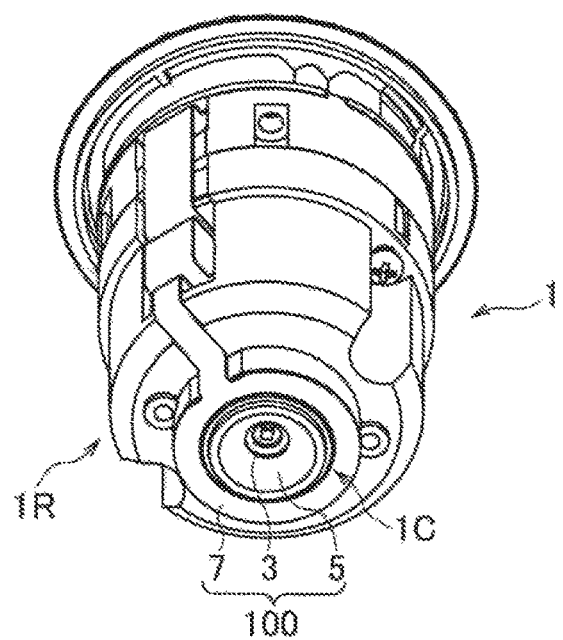
FIG. 2 is a perspective view of the infrared thermometer of FIG. 1 with a cover removed.

The proximity sensor 100 is arranged around the infrared sensor 3. The proximity sensor 100 includes an earth electrode (also referred to as "ground electrode") 5 and an outside counter electrode 7. FIG. 1 illustrates an exterior package 7a as a protecting part of the electrode 7, while FIG. 2 illustrates the electrode 7 being exposed with the exterior package 7a removed. The proximity sensor 100 is capable of sensing an approaching of the infrared sensor 3 to a measuring object portion of a human body or the like, contactlessly and exactly.

As can be seen from FIGS. 1 and 2, the mortar-shaped portion 1C constitutes the ground electrode 5 of the proximity sensor 100, while an annular portion around the ground electrode 5 constitute the electrode 7 of the proximity sensor 100.

Therefore, when measuring, for example, the body temperature of a baby, the measurer moves the mortar-shaped portion 1C (the apex portion 1B) of the infrared thermometer 1, which contains the infrared sensor 3, and the ground electrode 5 and the electrode 7 of the proximity sensor 100, closer to the skin of a human body. Thus, the proximity sensor 100 provided in the mortar-shaped portion 1C measures a distance between the sensor and the skin of the human body, while the infrared sensor 3 detects the infrared radiation from the human body in a non-contact manner to make the infrared thermometer 1 in no contact with the human's skin. Then, the body temperature can be measured from the quantity of so-detected infrared radiation.

The ground electrode 5 is disposed around the infrared sensor 3 and constitutes a sensor frame to stabilize a temperature of the infrared sensor 3 and reflect a radiation from a side surface. This sensor frame is used in place of the ground electrode 5, thereby ensuring a sufficient area as the ground electrode 5.

Figure 3A:
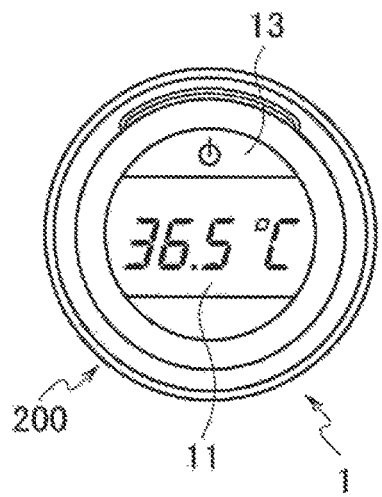
FIG. 3A is a rear view of the infrared thermometer according to the first embodiment, FIG. 3B a side view of the same infrared thermometer.

As illustrated in FIG. 3A, the infrared thermometer 1 is provided, on its rear surface, with a liquid crystal display unit 11 as a notification unit for displaying the body temperature or notifying a necessary alarm. The liquid crystal display unit 11 is provided, on its upper side, with a power switch 13 having a broad pressing surface. If the power switch 13 is operated and turned on, then the infrared thermometer 1 is activated to measure the body temperature in no contact with the measuring object portion of the human body and display the numerical value of the so-measured body temperature on the liquid crystal display unit 11.

Figure 3B:
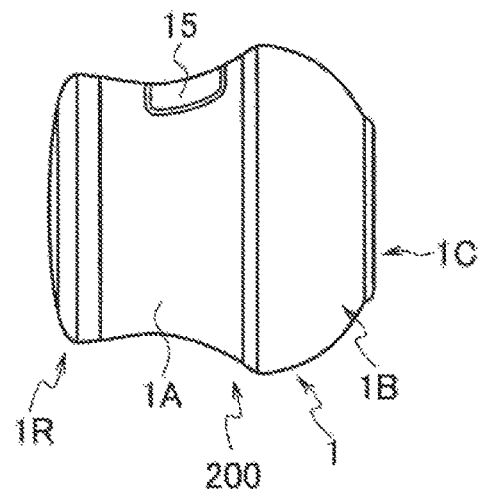
FIG. 3C is a front view of the same infrared thermometer.

Additionally, as illustrated in FIG. 3B, the cover 200 of the infrared thermometer 1 is provided, on a side surface of the concave portion 1A, with a battery housing part 15. Since the battery housing part 15 accommodates a battery, for example, a button battery with a voltage from 1.5 to 3 volts and additionally, a lid is fastened to the housing part by a screw, the same part functions as a power supply of the infrared thermometer 1 for its operable state.

Figure 3C:
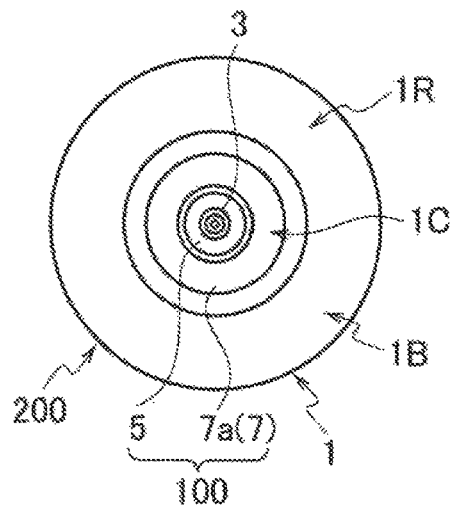

As illustrated in FIG. 3C, in the mortar-shaped portion 1C (the apex portion 1B) of the main unit 1R, there are concentrically arranged the infrared sensor 3, and the electrode 5 and the electrode 7 of the proximity sensor 100a around the infrared sensor 3.

Figure 4:
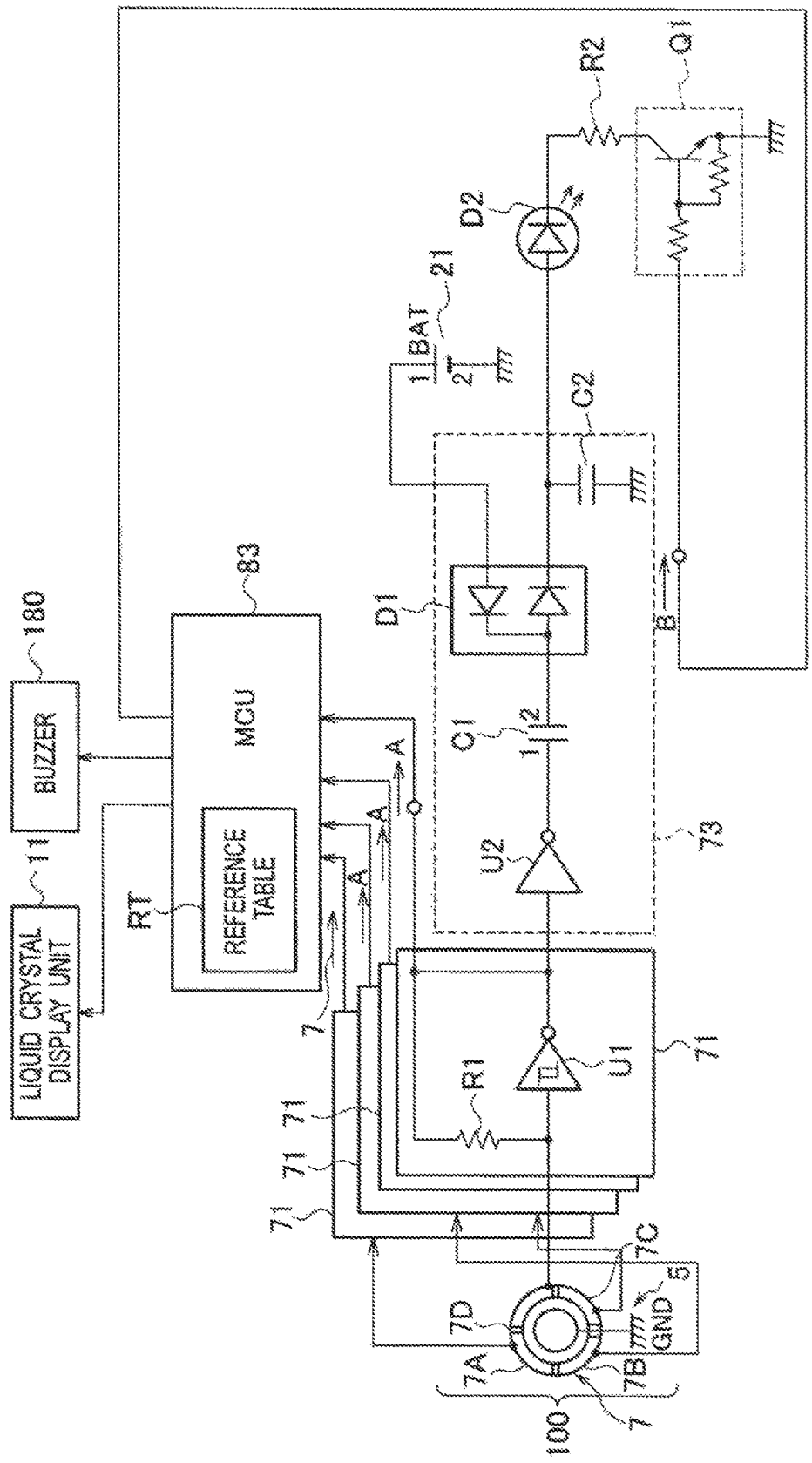
FIG. 4 is a circuit diagram illustrating a part of a circuit of the infrared thermometer according to the first embodiment.

A circuit illustrated in FIG. 4 includes a part of a measurement circuit for measuring the distance between the measuring object portion of the human body and the apex portion 1B (the mortar-shaped portion 1C of FIG. 3) of the infrared thermometer 1 with the proximity sensor 100 based on electrostatic capacitance detected by the proximity sensor 100, and a part of a circuit for notifying the completion of measuring the body temperature in the infrared thermometer 1 and also for lighting up a liquid-crystal backlight of the liquid crystal display unit 11.

The reason why an electrostatic capacity type sensor is used for the proximity sensor 100 is because it could be constructed by metal terminals, a wiring pattern provided on a substrate, a wiring pattern provided on a flexible substrate and so on, as long as sensor's electrode portions are made from electrically conductive materials. Due to a high degree of freedom in the profile of electrodes of the proximity sensor 100, additionally, it is easy to incorporate such electrodes in the thermometer and moreover, the measurement circuit is simple.

Figure 5:
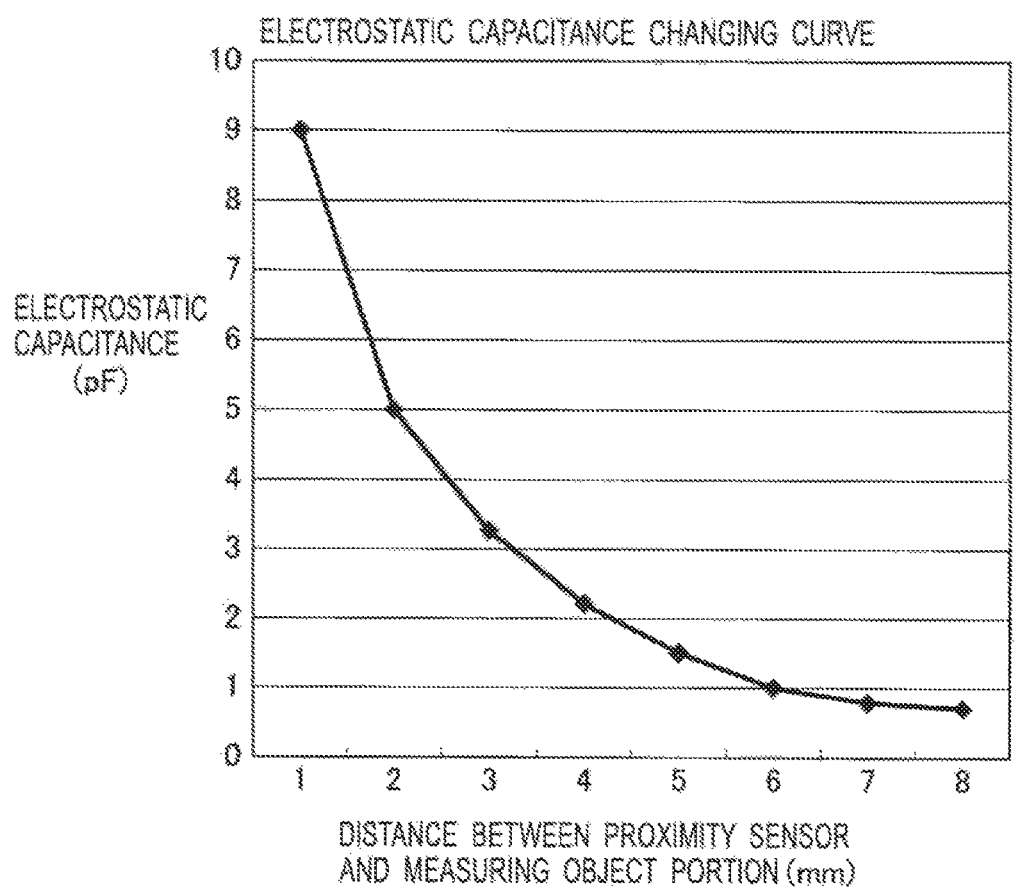
FIG. 5 is a graph of an electrostatic-capacitance change curve illustrating the relationship of electrostatic capacitance with respect to a distance between a proximity sensor used in the infrared thermometer according to the first embodiment and a measuring object portion.

As illustrated in FIG. 5, the electrostatic capacitance between the ground electrode 5 and the electrode 7 constituting the proximity sensor 100 changes under the influence of a distance between the proximity sensor 100 and the measuring object portion of the human body to which the proximity sensor 100 is getting access. When inputting the so-changeable electrostatic capacitance between the ground electrode 5 and the electrode 7 to an input of a Schmitt trigger CMOS inverter U1 having its input side connected to a resistance R1 as illustrated in FIG. 4, this Schmitt trigger CMOS inverter U1 oscillates at an oscillation frequency F explained with the equation (1).

$$F = 1/(0.8 \times Cf \times R1) \quad (1)$$

Here, Cf is an electrostatic capacitance which contains the electrostatic capacitance between the ground electrode 5 and the electrode 7 constituting the proximity sensor 100 and also a stray capacitance of wiring and which is the electrostatic capacitance changeable under the influence of the distance between the proximity sensor 100 and the measuring object portion of the human body to which the proximity sensor 100 is getting access. R1 is a resistance of a resistor R1 of FIG. 4.

In this way, an output signal A of the Schmitt trigger CMOS inverter U1 oscillating at the oscillation frequency F is fed to a microcontroller (MCU) 83 using a later-mentioned microprocessor. In the MCU 83, the oscillation frequency F is counted by a counter. Based on the count value of the oscillation frequency F, the distance between the human body and the proximity sensor 100 of the apex portion 1B of the infrared thermometer 1 is calculated.

When the proximity sensor 100 becomes closer to a human skin (e.g. forehead) as the measuring object portion, for example, when the sensor approaches a target within about 5 mm, the electrostatic capacitance C is proportional to the area of the electrode 7 of the proximity sensor 100 and inversely proportional to the distance between the sensor and the human skin as the measuring object portion, thereby taking a value close to the equation (2).

$$C = \varepsilon_0 \varepsilon_r S / 2t \, (F) \quad (2)$$

Here, S is the area of the electrode of the proximity sensor 100, t is the distance between the human skin as the measuring object portion and the proximity sensor 100, $\varepsilon_0$ is a dielectric constant in vacuum, and $\varepsilon_r$ is a relative dielectric constant (=1 in the air).

Incidentally, if the proximity sensor 100 moves away from the human skin etc. as the measuring object portion, the action of the proximity sensor 100 as a plane cannot be expected, so that the electrostatic capacitance decreases extremely. In such a case, the electrostatic capacitive of the proximity sensor 100 is nothing but a mere parameter proportional to the area of the electrode of the proximity sensor 100 and becomes equal to a sum of the stray capacitance of the wiring and the surface area of the electrode of the proximity sensor 100. As a result, even the distance between the sensor and the human skin etc. as the measuring object portion changes, the electrostatic capacitance would not change. Thus, in the distance range where the electrostatic capacitance does not change, the proximity sensor 100 is insensitive as a distance sensor and therefore, it can be said that the proximity sensor 100 is under a release state.

As illustrated in FIG. 4, the outside electrode 7 of the proximity sensor 100 is circumferentially divided into four segmented electrodes 7A, 7B, 7C, and 7D, which will be later-described in detail with reference to FIG. 10. The segmented electrodes 7A, 7B, 7C, 7D are connected to proximity-sensor circuits 71, respectively. The four proximity-sensor circuits 71 are connected to the MCU 83. The four proximity-sensor circuits 71 are adapted so as to supply the MCU 83 with output signals A of the Schmitt trigger CMOS inverters U1, respectively.

The reason why the outside electrode 7 is composed of the plurality of segmented electrodes 7A, 7B, 7C, 7D is to allow confirming whether or not the infrared thermometer 1 is inclined to the human skin, by measuring the distances between the human skin and the respective segmented electrodes 7A, 7B, 7C, 7D, thereby obtaining a tilt angle. In other words, the mortar-shaped portion 1C (the apex portion 1B) of the main unit 1R is constructed so as to detect a tilt angle of the sensor under condition that it is inclined to the human skin.

The infrared thermometer 1 is provided, as a notifying unit for notifying a measurer of the information or alarm, with the liquid crystal display unit 11 and a buzzer 180, as illustrated in FIG. 4. The liquid crystal display device 11 can notify, for example, a tilt angle with which the mortar-shaped portion 1C (the apex portion 1B) of the main unit 1R illustrated in FIG. 3C is inclined to the human skin, an alarm to be generated when this tilt angle exceeds a predetermined appropriate angle and a completion of measuring the body temperature.

By emitting a sound, additionally, the buzzer 180 can notify an alarm representing that, for example, this tilt angle has exceeded the predetermined appropriate angle and a situation where the measuring of the body temperature has been completed.

FIG. 5 is a graph of an electrostatic-capacitance change curve illustrating the relationship of electrostatic capacitance with respect to a distance t between the proximity sensor 100 and the measuring object portion. As illustrated in FIG. 5, when the distance t between the proximity sensor 100 and the measuring object portion becomes 5 mm or less, the electrostatic capacitance C is proportional to an area S of the electrode of the proximity sensor 100 and also inversely proportional to the distance t between the sensor and the measuring object portion, as indicated with the equation (2).

However, if the proximity sensor 100 moves away from the measuring object portion, the action of the proximity sensor 100 as a plane cannot be expected, so that the electrostatic capacitance decreases extremely.

Referring back to FIG. 4, the output signal A of the Schmitt trigger CMOS inverter U1 oscillating at the oscillation frequency F is supplied to MCU 83 where the distance t between the measuring object portion of the human body and the proximity sensor 100 is calculated. In addition, the output signal A of the Schmitt trigger CMOS inverter U1 is supplied to a booster circuit for raising 3 volts, which is the voltage of the battery housed in the battery housing part 15 illustrated in FIG. 3B, to the voltage of 6 volts for turning on a light emitting diode (LED), for example, a blue LED for the notification of the later-mentioned completion of measuring the body temperature.

That is, in FIG. 4, the output signal A of the above-mentioned Schmitt trigger CMOS inverter U1 is supplied, besides the MCU 83, to a CMOS inverter U2 where the signal is inverted and amplified to be a rectangular wave signal that repeats between the amplitude of the voltage E of 3 volts of the battery and 0 volt. Then, the rectangular wave signal is supplied to a capacitor C1. The capacitor C1 is charged by 3 volts of the voltage E of a battery 21 through a subsequent-stage Schottky diode D1.

That is, when the output of the CMOS inverter U2 is 0 volt, one terminal on the "2"-side of the capacitor C1 becomes a positive polarity, while another terminal on the "1"-side of the capacitor C1 becomes a negative polarity, so that 3 volts of the voltage E is charged to the capacitor C1.

Also, when the output of the CMOS inverter U2 is 3 volts of voltage E, the voltage 2E (voltage E×2=2E) of 6 volts, which is twice as much as the voltage E of 3 volts, is generated at the "2"-side terminal of the capacitor C1 since the voltage charged in the capacitor C1 is connected to the output of the CMOS inverter U2 in series. Then, the voltage 2E of 6 volts is charged to a capacitor C2 through the Schottky diode D1.

Thus, the voltage 2E (6 volts) charged to the capacitor C2 is supplied to a (e.g. blue) light emitting diode (LED) D2 for notifying the completion of measuring the body temperature measurement. A resistor R2 and a dimming transistor Q1 are connected to the light emitting diode D2 in series. A current flowing through the light emitting diode D2 is determined by the resistor R2. The ON/OFF of the dimming transistor Q1 is controlled by a dimming control signal B supplied from the MCU 83 to a base of the dimming transistor Q1. The light emitting diode is controlled so as to obtain the maximum brightness when the dimming transistor is turned on.

Figure 6:
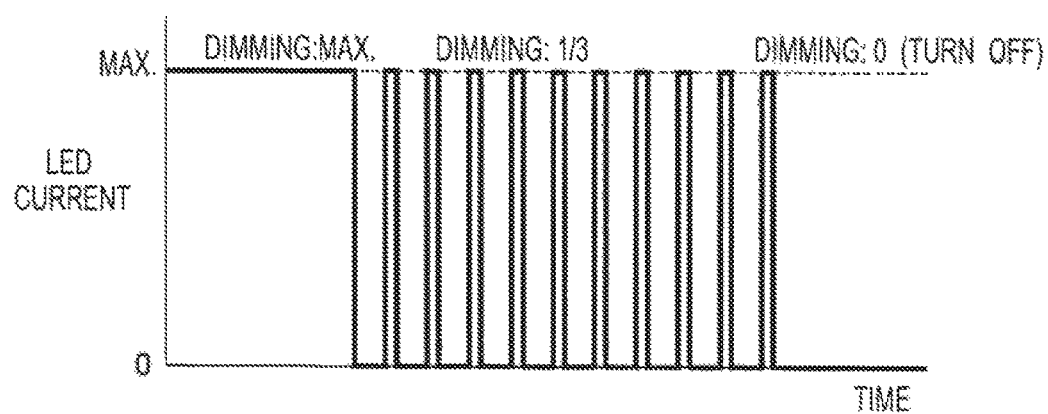
FIG. 6 is a diagram illustrating a current flowing through a light emitting diode (LED) used in the infrared thermometer according to the first embodiment and its dimming state.

In other words, due to the ON/OFF control of the dimming transistor Q1 through the dimming control signal B from the MCU 83, the current flowing through the light emitting diode D2 is controlled as illustrated in FIG. 6. Then, as illustrated in FIG. 6, when the current flows through the light emitting diode D2 continuously, the dimming is maximized. When the ON/OFF control is carried out, the dimming becomes one-third of the maximum. When the current is cut off, the light emitting diode D2 is turned off, so that the dimming becomes zero. The repetition period of the ON/OFF control whose dimming becomes ⅓ is set to an appropriate value giving no flickering of light to human eyes, for example, 1.6 ms or less. Note that the light emitting diode D2 is also used as a liquid-crystal backlight for the liquid crystal display unit 11. For use with this backlight, the light emitting diode D2 is adapted so as to be dimmable in multiple stages.

Figure 7:
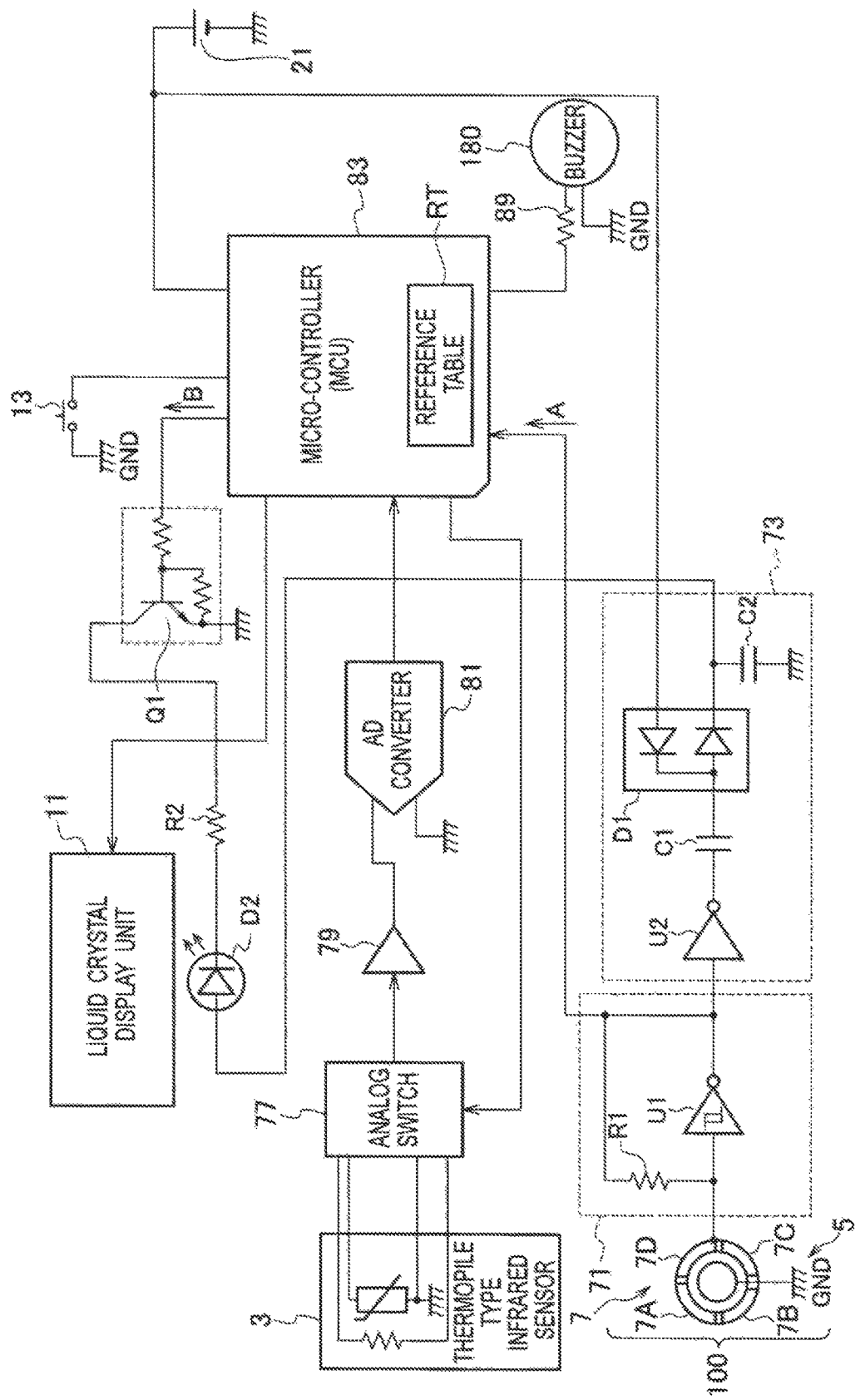
FIG. 7 is an overall circuit diagram of the infrared thermometer according to the first embodiment.

FIG. 7 is an overall circuit diagram of the infrared thermometer 1 according to the first embodiment, particularly, the entire circuit diagram of the infrared thermometer 1 of this embodiment including: a part of the measurement circuit for measuring the distance between the measuring object portion of the human body and the apex portion of the infrared thermometer 1 with the proximity sensor 100 based on the electrostatic capacitance detected by the above-mentioned proximity sensor 100; a part of the circuit for the notification function representing the completion of measuring the body temperature in the infrared thermometer 1 and also for the liquid-crystal backlight of the liquid crystal display unit 11; and the above-mentioned MCU 83.

In FIG. 7, incidentally, the above measurement circuit's part for measuring the distance t between the measuring object portion of the human body and the apex portion of the infrared thermometer 1 with the proximity sensor 100 based on the electrostatic capacitance C detected by the above-mentioned proximity sensor 100 is illustrated as a proximity-sensor circuit 71. A booster circuit for the above circuit's part for the notification function representing the completion of measuring the body temperature in the infrared thermometer 1 and also for the liquid-crystal backlight of the liquid crystal display unit 11 is illustrated as a backlight/illumination booster circuit 73.

In FIG. 7, there is illustrated only one proximity-sensor circuit 71 as a representative of four proximity-sensor circuits (oscillation circuits) 71 illustrated in FIG. 4, while three proximity-sensor circuits 71 are eliminated for simplification of the illustration.

As illustrated in FIG. 7, the output signal A of the Schmitt trigger CMOS inverter U1 from the sensor circuit 71 is fed to the MCU 83 to calculate the distance between the measuring object portion of the human body and the apex portion of the infrared thermometer 1 with the proximity sensor 100. From the MCU 83, the dimming control signal B is outputted to the dimming transistor Q1 by which the light emitting diode D2 is controlled through the resistor R2, thereby performing the dimming control and the backlight control for the liquid crystal constituting the liquid crystal display unit 11. The light emitting diode D2 is supplied with a voltage boosted up to 6 volts by the backlight/illumination booster circuit 73. The power switch 13 and the battery 21 of 3 volts are connected to the MCU 83.

As illustrated in FIG. 7, a thermopile type sensor composed of a plurality of thermocouples connected in series is used for the infrared sensor 3. The quantity of infrared measured by the thermopile-type infrared sensor 3 is amplified by an operational amplifier 79 through an analog switch 77 and subsequently converted into a digital signal by an AD converter 81. Then, the digital signal is supplied to the MCU 83. The MCU 83 calculates body temperature, i.e. temperature of the measuring object portion of the human body based on the digital signal from the infrared sensor 3 and displays the calculated body temperature on the liquid crystal display unit 11.

The infrared thermometer 1 includes, besides the blue light emitting diode D2, the buzzer 180 as the notification function representing the completion of measuring the body temperature measurement. The buzzer 180 is connected to the MCU 83 through a resistor 89, thereby sounding and informing the completion of measuring the body temperature under the control of the MCU 83.

Figure 8A:
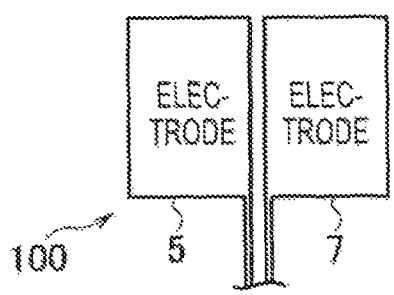
FIGS. 8A and 8B are conceptual diagrams illustrating a ground electrode (earth electrode) and another electrode etc. of the infrared thermometer according to the first embodiment.
Figure 8B:
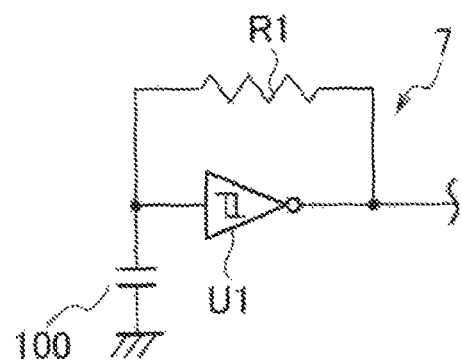
Figure 9:
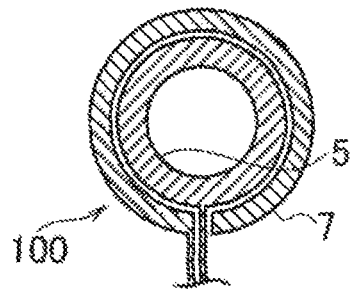
FIG. 9 is a view illustrating a shape example of the ground electrode and another electrode of the infrared thermometer according to the first embodiment.

Next, preferred structural examples of the proximity sensor 100 illustrated in FIGS. 4 and 7 will be described with reference to FIGS. 8 to 10. Although the proximity sensor 100 has been already illustrated in FIGS. 4 and 7, we now describe the structure of the proximity sensor 100 in more detail.

The proximity sensor 100 has a role as a distance meter for measuring the distance t between the proximity sensor 100 and the human skin. As illustrated in FIG. 8A, the proximity sensor 100 includes one pair of ground electrode 5 and electrode 7 having a certain area. The ground electrode 5 and the electrode 7 are arranged on a plane, in proximity to each other. Between the ground electrode 5 and the electrode 7, there is an electrostatic capacitance C which is proportional to the area S. The electrostatic capacitance C becomes larger as the broader the area S of the electrodes is larger.

The MCU 83 obtains a value of the electrostatic capacitance C by counting an oscillating number per unit time obtained from the proximity-sensor circuit 71. As the proximity sensor circuit 71 produces an error in the count number due to an interference by electromagnetic wave as external noise, it is desirable to ensure the area of the ground electrode 5 and the outside electrode 7 (the segmented electrodes 7A, 7B, 7C, 7D) as large as possible (lowering frequency) while using a noise-removal software together, thereby improving the S/N ratio. Nevertheless, because there is a limit to the area incorporable into the infrared thermometer 1 and additionally, the sampling has to be performed in a moment, it would be less desirable to adopt a software enabling a sophisticated noise reduction.

When the skin of the human body as an electrical conductor approaches the proximity sensor 100, the electrostatic capacitance between the ground electrode 5 and the electrode 7 increases, while the oscillating number per unit time decreases. The larger the area of the ground electrode 5 and the electrode 7 is, the larger the electrostatic capacitance gets. Accordingly, if it is within the area range of the ground electrode 5 and the electrode 7 that can be used for the infrared thermometer 1, the distance from the sensor up to the human skin can be obtained by the rate of change from the release state of the proximity sensor 100, without affecting the magnitude of the electrostatic capacitance.

"The release state of the proximity sensor 100" is used to refer to such a condition that, during the period from the power supply of the infrared thermometer 1 until the access of the infrared thermometer 1 to the human skin, the infrared thermometer 1 is so far away from the human skin as to be outside the predetermined designed-measurement distance range of the proximity sensor 100, namely, a situation where the oscillating frequency F becomes a constant value. With the subsequent access of the infrared thermometer 1 to the human skin, when the human skin enters the predetermined designed-measurement distance range of the proximity sensor 100 to cause the oscillating frequency F to be changed from a so-called "open value in the oscillating frequency F" in the release state, the Schmitt trigger CMOS inverter U1 supplies an output signal A whose oscillating frequency F changes to the MCU 83 for counting the oscillating number. Then, based on the counting result, the MCU 83 calculates the distance between the measuring object portion and the apex portion of the infrared thermometer 1.

The MCU 83 includes a reference table RT. The MCU 83, as a controller, acquires a first distance between the measuring object portion (e.g. forehead skin) and the segmented electrode 7A of the electrode 7 of the proximity sensor 100, a second distance between the measuring object portion (e.g. forehead skin) and the segmented electrode 7B of the electrode 7 of the proximity sensor 100, a third distance between the measuring object portion (e.g. forehead skin) and the segmented electrode 7C of the electrode 7 of the proximity sensor 100, and a fourth distance between the measuring object portion (e.g. forehead skin) and the segmented electrode 7D of the electrode 7 of the proximity sensor 100.

Thus, by comparing the first distance to the fourth distance with each other, the MCU 83 judges, when measuring the body temperature with use of the infrared thermometer 1, whether or not the mortar-shaped portion 1C (the apex portion 1B) of the main unit 1R of the infrared thermometer 1 is directed to the human skin in an appropriate posture, by the tilt angle of the mortar-shaped portion 1C. Then, if the mortar-shaped portion 1C of the main unit 1R is inclined to the human skin within a predetermined appropriate tilt-angle range, then the MCU 83 refers to the reference table RT and corrects the measured body temperature depending on the magnitude of the tilt angle of the mortar-shaped portion 1C of the main unit 1R to the human skin, thereby enabling a more accurate body temperature to be measured. That is, depending on the tilt angle of the infrared thermometer 1 to the human skin, the measurement area between the ground electrode 5 and each of the segmented electrodes 7A, 7B, 7C, 7D of the proximity sensor 100 changes to affect a measurement of the body temperature. Therefore, the measured body temperature has to be corrected in accordance with the magnitude of the tilt angle when the mortar-shaped portion 1C is inclined to the human skin.

In this way, depending on the tilt angle of the infrared thermometer 1 to the human skin, the measurement area between the ground electrode 5 and each of the segmented electrodes 7A, 7B, 7C, 7D of the proximity sensor 100 changes to affect a measurement of the body temperature. For this reason, it is necessary to correct the measurement of the body temperature by referring to the reference table RT.

Figure 10:
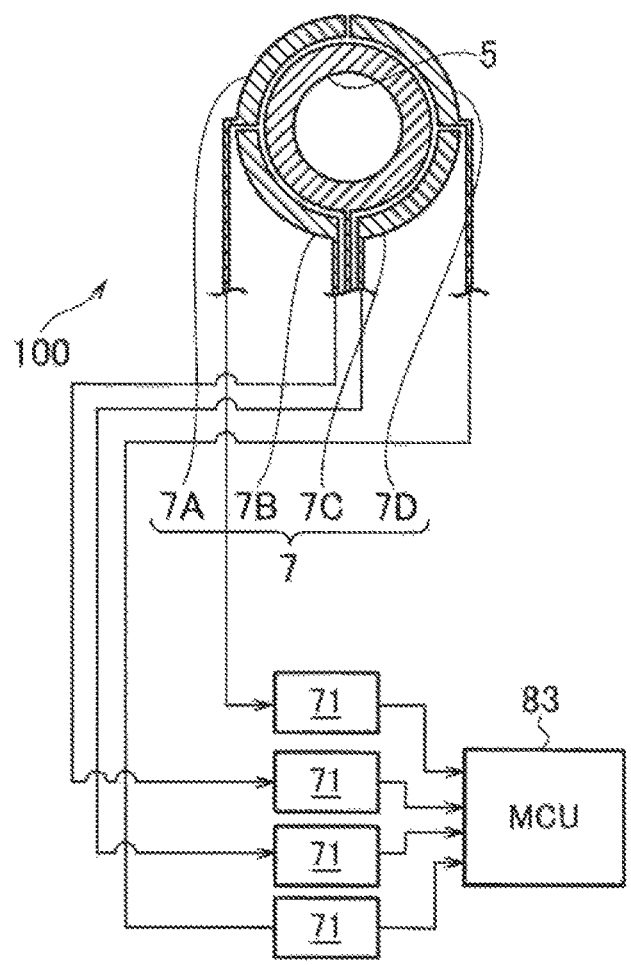
FIG. 10 is a view illustrating a preferable shape example of the ground electrode and the electrode in the infrared thermometer according to the first embodiment.

As illustrated in FIG. 10, the outside electrode 7 of the proximity sensor 100 is segmented to four segmented electrodes 7A, 7B, 7C, 7D by dividing it in the circumferential direction. Then, by grasping the distance at each unit location of the segmented electrodes, it becomes possible to grasp whether or not the tilt angle (posture) of the infrared thermometer 1 to the skin is appropriate for the measurement of body temperature.

To obtain the distance between the infrared sensor 3 of the mortar-shaped portion 1C (the apex portion 1B) of the main unit 1R of the infrared thermometer 1 and the human skin, as illustrated in FIG. 10, it is preferable that the ground electrode 5 and the electrode 7 of the proximity sensor 100 are arranged in an outer circumferential area (peripheral part) of the infrared sensor 3 doubly and concentrically. The ground electrode 5 is disposed on the inside of the sensor, while the electrode 7 is disposed on the outside concentrically. By using the proximity sensor 100, the MCU 83 is capable of measuring the body temperature in a non-contact state keeping a certain distance from the human skin.

Next, the operation of the above-constructed infrared thermometer 1 will be described.

First, when turning on the power switch 13 of the infrared thermometer 1 to supply an operating voltage from the 3 volts battery 21 in the battery housing part 15 to the infrared thermometer 1, the infrared sensor 3 and the proximity sensor 100 of the infrared thermometer 1 start their operation.

Then, when measuring the distance between the human skin and the infrared thermometer 1, a measurer pinches the concave portion 1A of the mortar-shaped infrared thermometer 1 by fingers etc. and moves the mortar-shaped portion 1C (the apex portion 1B) of the main unit 1R of the infrared thermometer 1 closer to the human body, for example, a forehead skin.

Then, the MCU 83 measures the first distance to the fourth distance between the measuring object portion and the proximity sensor 100 based on the electrostatic capacitances between the ground electrode 5 and the segmented electrodes 7A, 7B, 7C, 7D of the electrode 7 of the proximity sensor 100 in the mortar-shaped portion 1C (apex portion 1B). In detail, the proximity sensor 100 measures the first distance between the measuring object portion (e.g. forehead skin) and the segmented electrode 7A of the electrode 7 of the proximity sensor 100, the second distance between the measuring object portion (e.g. forehead skin) and the segmented electrode 7B of the electrode 7 of the proximity sensor 100, the third distance between the measuring object portion (e.g. forehead skin) and the segmented electrode 7C of the electrode 7 of the proximity sensor 100, and the fourth distance between the measuring object portion (e.g. forehead skin) and the segmented electrode 7D of the electrode 7 of the proximity sensor 100.

During the period from the power supply of the infrared thermometer 1 until the access of the infrared thermometer 1 to the human skin, there always exists a release state of the proximity sensor 100 where the oscillating frequency F becomes a constant value since the infrared thermometer 1 is so far away from the human skin as to be outside the predetermined designed-measurement distance range of the proximity sensor 10. Therefore, provided that an identical value is maintained in the oscillating frequency F, the MCU 83 holds it as "open value in the oscillating frequency F".

If the values from the first distance to the fourth distance are included in the predetermined designed-measurement distance range of the proximity sensor 10, the MCU 83 judges that it is possible to measure the body temperature. Then, the MCU 83 displays that it is possible to measure the body temperature the body temperature on the liquid crystal display unit 11 and notifies it to the measurer.

With the subsequent access of the infrared thermometer 1 to the human skin, when the human skin enters the predetermined designed-measurement distance range of the proximity sensor 100 to cause the oscillating frequency F to be changed from this "open value in the oscillating frequency F" in the release state, the Schmitt trigger CMOS inverter U1 supplies an output signal A whose oscillating frequency F changes to the MCU 83 for counting the oscillating number. Then, based on the counting result, the MCU 83 calculates the distance between the measuring object portion and the apex portion of the infrared thermometer 1.

The MCU 83 displays that the infrared thermometer 1 has approached the human skin and thus entered in the predetermined designed-measurement distance range of the proximity sensor 100, on the liquid crystal display unit 11 to inform a "body-temperature measuring state". Moreover, the MCU 83 as the controller acquires the first distance between the measuring object portion (e.g. forehead skin) and the segmented electrode 7A of the electrode 7 of the proximity sensor 100, the second distance between the measuring object portion (e.g. forehead skin) and the segmented electrode 7B of the electrode 7 of the proximity sensor 100, the third distance between the measuring object portion (e.g. forehead skin) and the segmented electrode 7C of the electrode 7 of the proximity sensor 100, and the fourth distance between the measuring object portion (e.g. forehead skin) and the segmented electrode 7D of the electrode 7 of the proximity sensor 100, and also compares the first distance to the fourth distance with each other.

Thus, the MCU 83 judges whether or not the mortar-shaped portion 1C (the apex portion 1B) of the main unit 1R of the infrared thermometer 1 is directed to the human skin at an appropriate tilt angle. Then, in use of the infrared thermometer 1, if the main unit 1R is inclined to the human skin within the predetermined appropriate tilt-angle range, then the MCU 83 refers to the reference table RT and corrects the measured body temperature depending on the magnitude of the tilt angle, thereby enabling a more accurate body temperature to be measured.

Incidentally, as the infrared thermometer 1 is a non-contact type, the measurer is ignorant of the time when the body temperature was measured or whether or not the body temperature has not been measured yet. Therefore, if the body-temperature measurement was successful fairly, the MCU 83 actuates the buzzer 180 for its sounding. Accordingly, the measurer can recognize that the body-temperature measurement was successful, reliably.

Thus, by using the proximity sensor 100, the infrared thermometer 1 can measure the distance up to the human body as a subject and further detect the body temperature at an optimum distance contactlessly.

If the tilt angle of the mortar-shaped portion 1C (the apex portion 1B) of the main unit 1R is greater than the appropriate tilt-angle range, it is desirable that the MCU 83 allows the buzzer 180 to be sounded to call a measurer's attention to correcting of the tilt angle of the infrared thermometer 1 to the human skin so that the infrared thermometer 1 takes a correct vertical posture (direction) to the human skin. Additionally, the MCU 83 can allow the liquid crystal display unit 11 to display that the infrared thermometer 1 is being inclined at an inadequate tilt angle and furthermore, an instruction item to change the present angle to an appropriate tilt angle.

At the point in time when the mortar-shaped portion 1C (the apex portion 1B) of the main unit 1R is directed to the human skin at an appropriate tilt angle, the MCU 83 acquires the tilt angle and the distance between the infrared thermometer 1 and the human skin and subsequently corrects the body temperature by using the "for-correction" reference table with respect to each tilt angle, which is prepared in advance, thereby enabling an appropriate measurement of the body temperature to be performed. The body temperature measured with use of the infrared sensor 3 can be displayed on the liquid crystal display unit 11. The completion of measuring the body temperature can be notified to the measurer by lighting up the blue light emitting diode D2 and further sounding the buzzer 180.

Incidentally, when the temperature measured with use of the infrared sensor 3 is more than 28° C., this temperature can be regarded as the body temperature of the measuring object portion in the human body. However, if the temperature is less than 28° C., then it is ignored on the assumption that the infrared thermometer may touch any object (e.g. clothes, hair) other than the human body or the infrared thermometer may be placed on a desk.

Again, although the infrared sensor 3 is responsive to conductive materials, it does not react to such as a desk made from wood, plastic, or the like. Furthermore, the infrared sensor 3 reacts to a such as desk made from metal or the like. Nevertheless, when the room temperature is not high, the temperature at this time is be ignored since it desk does not become as high as the body temperature.

As described above, according to the first embodiment, the infrared sensor 3 of the infrared thermometer 1 is capable of measuring the body temperature while avoiding the contact with the human skin, namely, contactlessly. For this reason, as the infrared thermometer 1 does not touch the human skin as a subject being inspected, such as a baby, there is no transfer in temperature during the contactless body-temperature measurement, thereby allowing the body temperature to be measured more precisely.

In the first embodiment, the infrared sensor 3 of the infrared thermometer 1 measures the body temperature contactlessly with the human skin and displays the body temperature on the liquid crystal display unit 11. Therefore, it is very effective in measuring the body temperature of a baby or an infant who is apt to be constantly on the move when measuring the body temperature, for example, a subject turning its back and refusing the measurement. That is, as such as an infant or baby moves its face reflexively as soon as an object touches, it is very effective that the infrared thermometer 1 according to the first embodiment can measure the body temperature contactlessly and it is possible to measure the body temperature of such as an infant without failure, reliably and simply.

Additionally, the infrared thermometer 1 has also a function of converting the temperature of a forehead surface to the temperature of an underarm for display. Then, it is necessary to measure the temperature of the forehead surface at a specific location, such as a forehead's center. This is because there is a need of measuring the temperature derived from an artery in the vicinity of this region.

The infrared thermometer 1 according to the first embodiment employs the infrared sensor 3 to measure the body temperature in non-contact with a human body, and includes the proximity sensor 100 for detecting that the main unit 1R incorporating the infrared sensor 3 has approached the human body, and the controller (MCU) 83 for calculating the body temperature of the human body based on the quantity of infrared from the infrared sensor 3 when the proximity sensor 100 detects that the main unit 1R has approached the human body. The proximity sensor 100 includes the ground electrode 5 and the multiple segmented electrodes 7 (7A, 7B, 7C, 7D) disposed around the grounding electrode 5, and the controller 83 is constructed so as to measure the electrostatic capacitances between the ground electrode 5 and the respective segmented electrodes 7A, 7B, 7C, 7D when approaching the human body and also measure the distance between the main unit 1R and the human body based on the electrostatic capacitances, thereby detecting an inclination of the main unit 1R to the human body.

Thus, since the tilt angle of the main unit to the human body is detected without touching the skin of the human body as the subject (e.g. a baby), there is no transfer of the body temperature during the measurement of the body temperature in a non-contact state, so that it is possible to measure the body temperature precisely with a precise orientation of the main unit's posture to the human body.

The controller (MCU) 83 includes the reference table RT for correcting the measured body temperature and corrects the previously measured temperature by referring to the reference table RT from the obtained tilt angle. Even if the main unit is inclined to the human body, the controller (MCU) 83 is capable of correcting the measured body temperature corresponding to the tilt angle by referring to the reference table RT and therefore, it is possible to measure the body temperature more precisely.

The ground electrode 5 of the proximity sensor 100 is formed into a ring shape, while the multiple segmented electrodes 7 (7A, 7B, 7C, 71D) are formed by dividing a ring-shaped electrode on the outside of the ground electrode 5. Thus, since the electrostatic-capacitance type proximity sensor 100 has a structure including the ground electrode and the multiple segmented electrodes, there is ensured a degree of freedom in design, so that the proximity sensor is easily incorporated in an infrared thermometer.

The infrared thermometer includes the liquid crystal display unit 11 as a notification unit that notifies such a situation that the tilt angle of the main unit to the human body exceeds a predetermined tilt angle and also notifies a completion of measuring the body temperature. Accordingly, a measurer can recognize that the main unit is being inclined to the human in an inappropriate posture through the notification unit. Additionally, the measurer can recognize a situation where the measurement of the body temperature has been completed, certainly by a notification through the notification unit.

Although one example of the present application has been illustrated hereinbefore, needless to say, the present application may be modified in any way.

Figure 11:
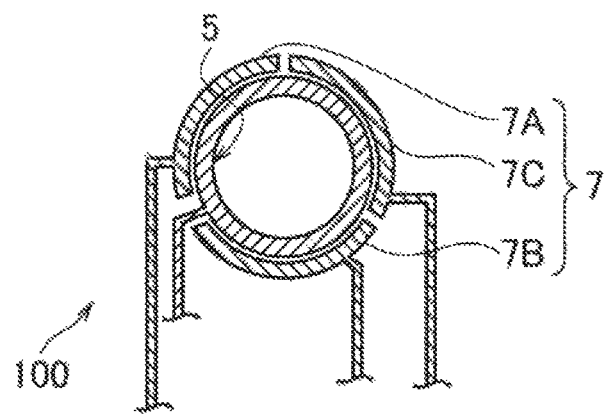
FIG. 11 is a view illustrating another preferable shape example of the ground electrode and the electrode in the infrared thermometer according to the first embodiment.

For example, FIG. 11 illustrates a geometrical example of the ground electrode 5 and the outside electrode 7 according to a modification of the first embodiment. By dividing in the circumferential direction, the outside electrode 7 of the proximity sensor 100 is segmented to three segmented electrodes 7A, 7B, 7C as illustrated in FIG. 11. Then, the main unit of the infrared thermometer 1 can detect a tilt angle to the skin by grasping respective distances at each unit position of the segmented electrodes and consequently correct the body temperature.

Figure 12:
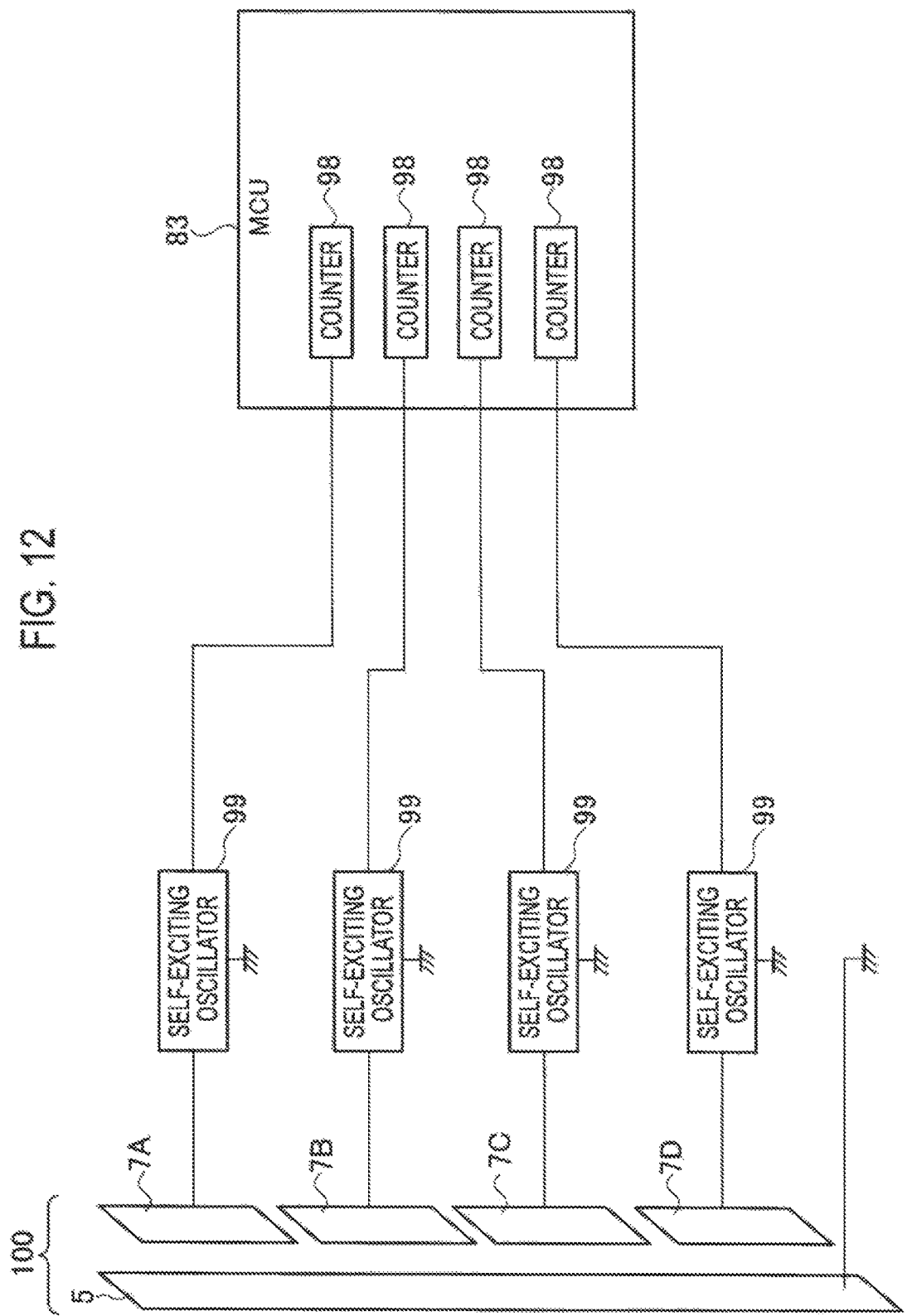
FIG. 12 is a diagram illustrating a general example of connection between four segmented electrodes and an MCU of the infrared thermometer according to the first embodiment.

FIG. 12 illustrates a general connection example between four segmented electrodes 7A, 7B, 7C, 7D and the MCU 83. Each of the segmented electrodes 7A, 7B, 7C, 7D is connected to a counter 98 in the MCU 83 through a self-exciting oscillator 99.

The notification unit may be formed by an organic EL display unit, a speaker, or the like without being limited to the liquid crystal display unit 11 or the buzzer 180.

Second Embodiment

An infrared thermometer 1 according to a second embodiment will be described with reference to FIGS. 13 to 27.

Figure 13:
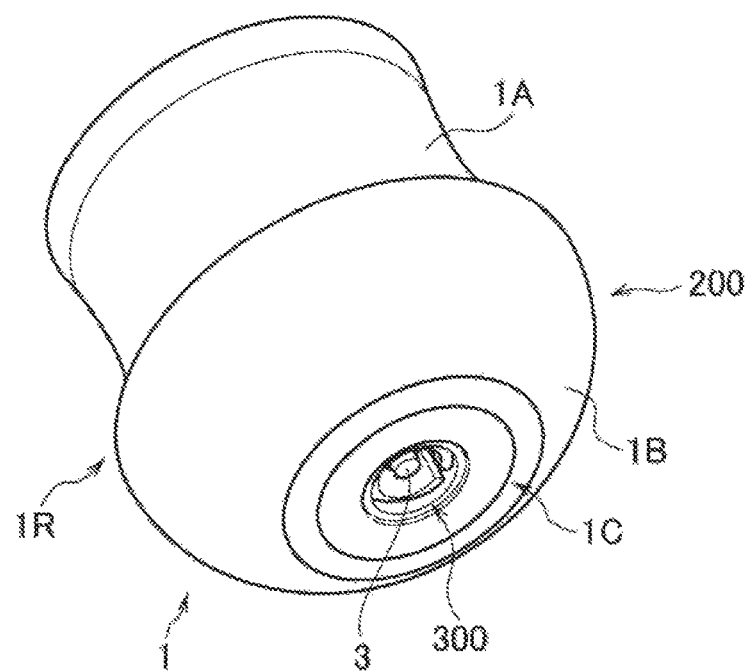
FIG. 13 is a perspective view of an infrared thermometer according to a second embodiment.

As illustrated in FIG. 13, the infrared thermometer 1 according to the second embodiment includes the cover 200. The cover 200 is configured so as to be slightly-vertical barrel-shaped. Owing to this configuration, it is easy for a measurer to pinch the concave portion 1A etc. which is slightly recessed at the center of the cover 200, by fingers. Then, the measurer is supposed to pinch the concave portion 1A of the cover 200 of the infrared thermometer 1 and also measure a body temperature in no contact, at a position closer to a measuring target whose body temperature is to be measured, for example, a human skin positioned at the central part of a forehead of a human body, such as a baby's body.

Consequently, the infrared thermometer 1 is in no contact with the human skin. In other words, as the infrared thermometer does not touch a skin of a human body (e.g. baby) as a subject being inspected, there is no possibility that heat (body temperature) is transferred from the skin to the infrared thermometer 1, so that it is possible to measure more accurate body temperature.

As illustrated in FIG. 13, the substantially central portion of the front side of a main unit 1R of the infrared thermometer 1, that is, the substantially central portion of the apex portion 1B of the cover 200, which is directed downward to the right as illustrated in FIG. 13, is recessed in a mortar shape to constitute the mortar-shaped portion 1C. The infrared sensor 3 and a distance sensor 300 are attached to the recessed portion at the center of the mortar-shaped portion 1C.

Figure 14:
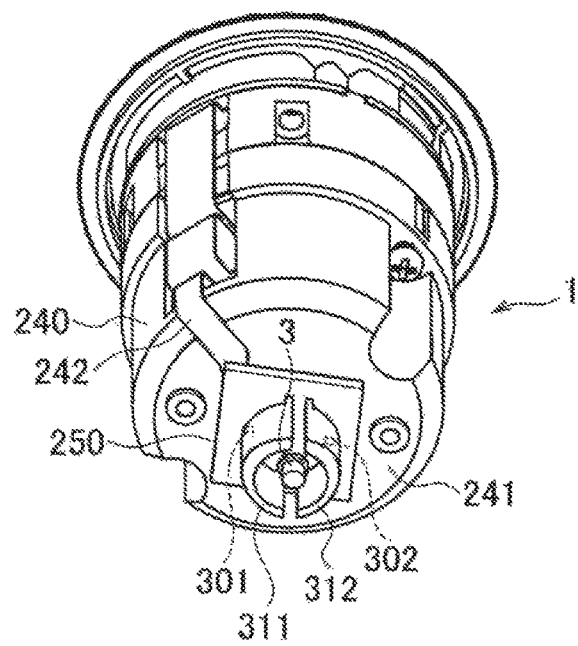
FIG. 14 is a perspective view of the infrared thermometer cover according to the second embodiment with a cover removed.

As illustrated in FIG. 14, a circuit board 250 is disposed inside the apex portion 1B of the infrared thermometer 1. The circuit board 250 is equipped with the infrared sensor 3 for measuring the body temperature and the distance sensor 300 for measuring the distance between the measuring object portion of the human body and the apex portion 1B of the infrared thermometer 1. In the circuit board 250, the distance sensor 300 is arranged around the infrared sensor 3.

As illustrated in FIG. 14, the circuit board 250 is fixed to a leading end 241 of an inner structure 240. That is, the circuit board 250 is arranged in the apex portion 1B of the main unit 1R. Thus, it is possible to orientate the distance sensor 300 and infrared sensor 3 on the circuit board 250 to the measuring object portion of the human body, for example, a baby's forehead skin, easily without being disturbed by other elements. Therefore, it is possible to measure the distance between the leading end 241 of the inner structure 240 and the human skin, such as a forehead, and the quantity of infrared from the human skin (e.g. forehead) directly.

The circuit board 250 is electrically connected to a controller (the controller 150 illustrated in FIG. 17) arranged in the inner structure 240 with use of e.g. a flexible wiring board 242. The distance sensor 300 can detect an approach distance of the infrared sensor 3 to the measuring object portion of the skin, such as a forehead of the human body, contactlessly and precisely.

The distance sensor 300 is also called to as "distance measuring sensor". For example, when measuring the body temperature of a baby, the measurer moves the infrared sensor 3 and distance sensor 300 of the infrared thermometer 1 closer to the skin, such as a human forehead. Thus, in a position where the distance sensor 300 provided in the mortar-shaped portion 1C has measured the distance between the sensor and the human skin precisely, the quantity of infrared from the human body is detected by the infrared sensor 3 in a non-contact state of not allowing the infrared thermometer 1 to make contact with the human skin. The body temperature can be obtained since the controller calculates the body temperature from the quantity of infrared detected.

Figure 15A:
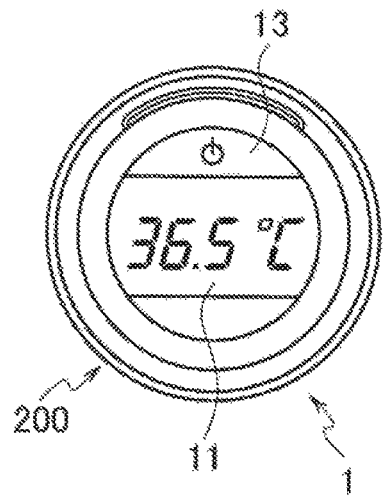
FIG. 15A is a rear view of the infrared thermometer according to the second embodiment, FIG. 15B a side view of the same infrared thermometer.

As illustrated in FIG. 15A, the infrared thermometer 1 is provided, on its rear surface, with the liquid crystal display unit 11 as a notification unit for displaying the body temperature and notifying a necessary alarm. The liquid crystal display unit 11 is provided, on its upper side, with the power switch 13 having a broad pressing surface. If the power switch 13 is operated and turned on, then the infrared thermometer 1 is activated to measure the body temperature in no contact with the measuring object portion of the human body and display the numerical value of the so-measured body temperature on the liquid crystal display unit 11.

Figure 15B:
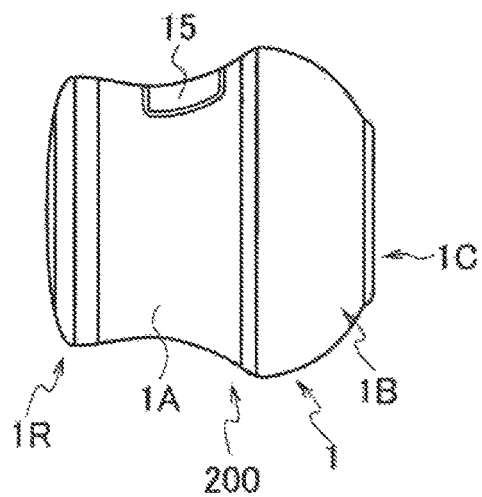
FIG. 15C is a front view of the same infrared thermometer.

As illustrated in FIG. 15B, the cover 200 of the infrared thermometer 1 is provided, on a side surface of the concave portion 1A, with the battery housing part 15. By accommodating a battery (i.e. a battery 221 illustrated in FIG. 17), such as a button battery with a voltage from 1.5 volts to 3 volts, in the battery housing part 15 and subsequently fasting a lid to the housing part by a screw, the resulting arrangement functions as a power supply of the infrared thermometer 1, so that it becomes operable.

Figure 15C:
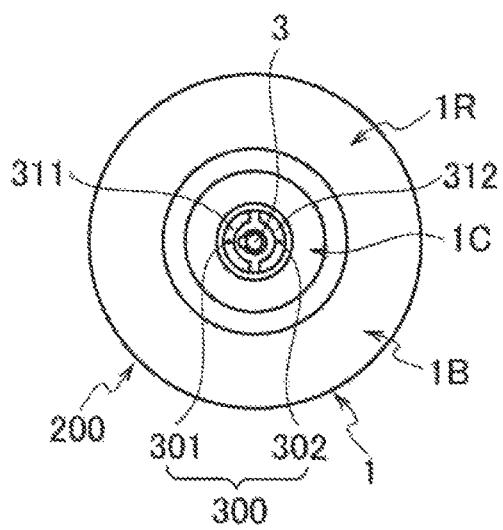

As illustrated in FIG. 15C, in the mortar-shaped portion 1C (the apex portion 1B) of the main unit 1R, there are concentrically arranged the infrared sensor 3 and the distance sensor 300 around the infrared sensor 3.

Next, a preferred structural example of the distance sensor 300 will be described with reference to FIGS. 16 to 21, in detail.

Figure 16:
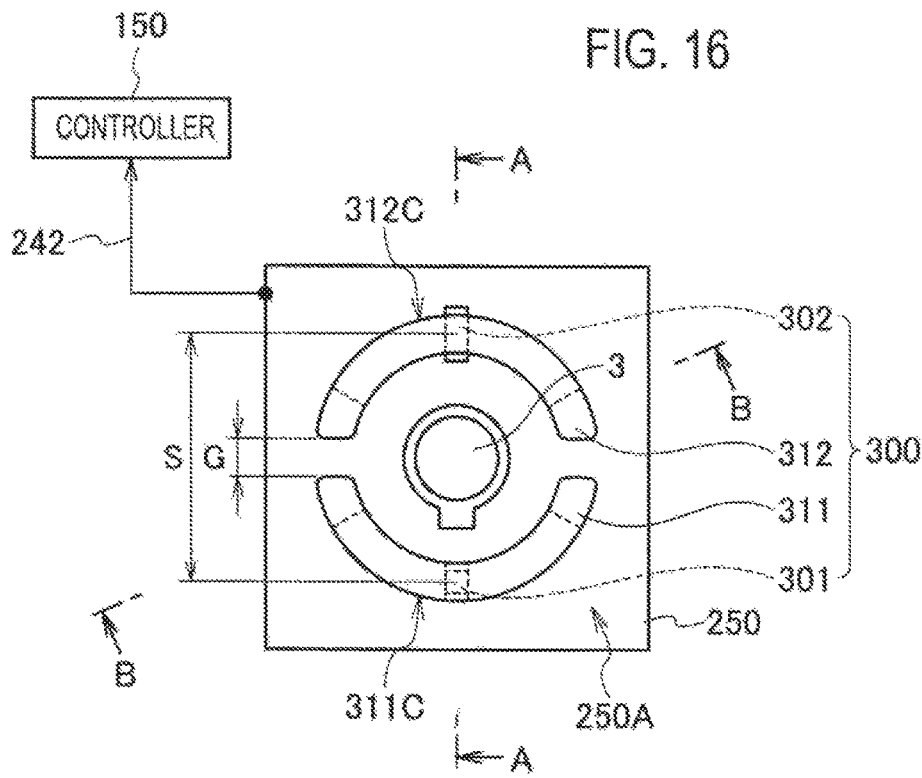
FIG. 16 is a front view illustrating a circuit board on which a distance sensor and an infrared sensor of the infrared thermometer according to the second embodiment are mounted.
Figure 17:
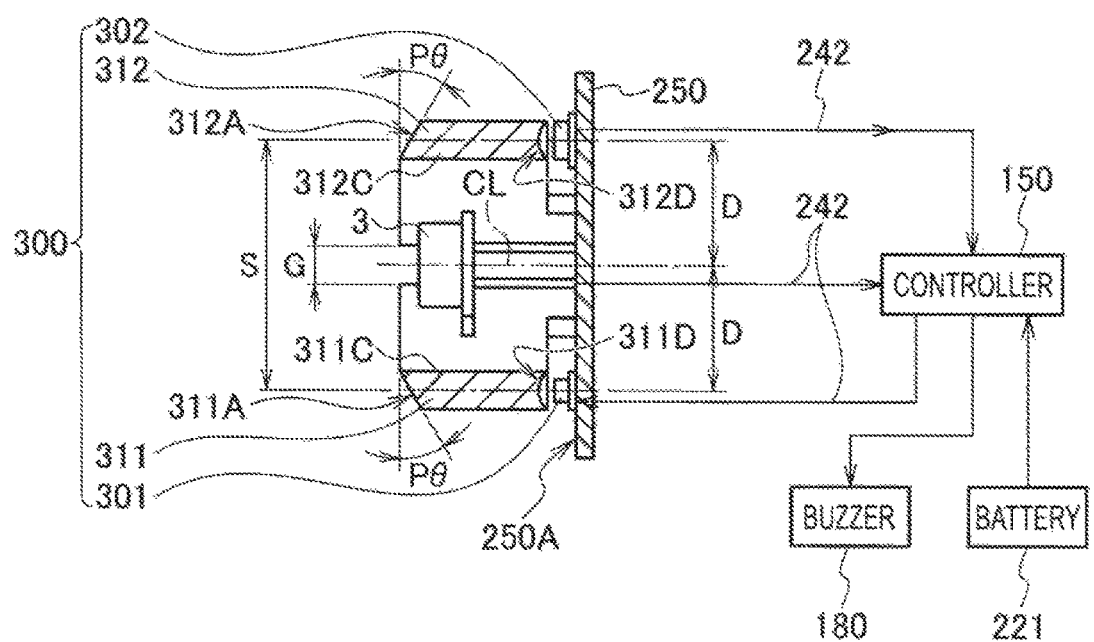
FIG. 17 is a cross sectional view taken along a line A-A of FIG. 16.

As illustrated in FIG. 16, the distance sensor 300 for distance measurement and the infrared sensor 3 for temperature measurement are mounted on one surface 250A of the circuit board 250. As illustrated in FIG. 17, the circuit board 250 is electrically connected to the controller 150 by use of a flexible wiring board 242. Although the illustrated circuit board 250 is formed by e.g. a square-shaped substrate, the shape of the circuit board 250 may be circular alternatively. The infrared sensor 3 is fixed to the circuit board 250 at its center position and along a center axis CL. The distance sensor 300 is fixed, around the infrared sensor 3, to the circuit board concentrically with the infrared sensor 3, around the center axis CL as a center.

Incidentally, although a conventional thermometer for measuring the body temperature in a direct-contact state with a skin has a constant measurement distance due to its direct contact with the skin, the transfer of a heat occurs between a thermometer's main body and the skin, causing an error to be contained in a value to be measured originally.

Therefore, the infrared thermometer 1 according to the second embodiment requires the distance sensor 300 for measuring the distance up to the skin in a non-contact state in view of measuring the body temperature at a given distance from the skin in a non-contact state. If leaving the measurement distance to a measurer's procedure, such a method could be a factor of producing an error in the measured value when measuring the body temperature. Therefore, in order to eliminate the factor of producing this error, the infrared thermometer 1 is adapted so as to be enable a distance between the main unit 1R and the human skin (target TG) to be precisely measured by the distance sensor 300, as illustrated in FIG. 21.

Figure 21:
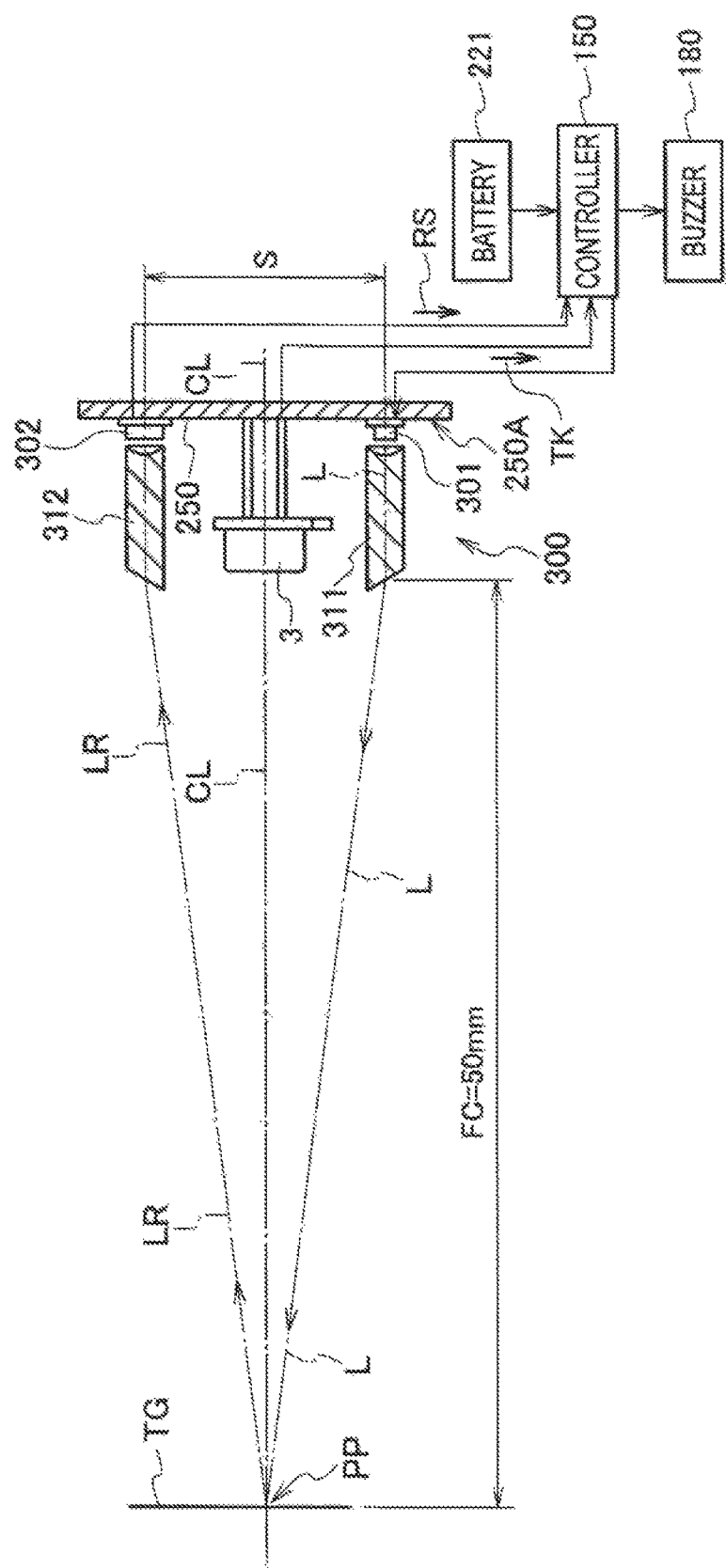
FIG. 21 is a diagram illustrating a situation of the infrared thermometer according to the second embodiment where light of a light source is projected onto the target and subsequently received, as return light, by a light receiving sensor.

As illustrated in FIG. 21, the distance sensor 300 is an optical sensor and projects light L to a skin as the target TG. Then, a light receiving sensor 302 receives the quantity (intensity) of return light LR (reflection light) of the light L and transmits a light reception signal RS to the controller 150. Accordingly, the controller 150 calculates a measurement distance from the magnitude of a signal-level value of the light reception signal RS based on the magnitude of the quantity of return light LR.

As illustrated in FIG. 16, the distance sensor 300 includes a light source 301, the light receiving sensor 302, a projector lens 311, and a light receiving lens 312. As illustrated in FIG. 17, the light source 301 and the light receiving sensor 302 are secured at mutually-opposed symmetrical positions by pinching the infrared sensor 3. A distance D between the light source 301 and the infrared sensor 3 and a distance D between the light receiving sensor 302 and the infrared sensor 3 (=S/2) are set equal to each other. In FIG. 21, an arrangement interval between the light source 301 and the light receiving sensor 302 is indicated with "S". Although the arrangement interval S takes a value of e.g. 12 mm, the value is not particularly limited.

For example, a light emitting diode (LED) may be used as the light source 301. For the light that the light source 301 emits, it is desirable to use near-infrared light other than visible light in order to facilitate a distinction from external light as disturbance light. For the light receiving sensor 302, there is available, for example, a photodiode capable of receiving the near-infrared light. Preferably, the light source 301 is not turn on all the time but flashes at regular intervals.

In this case, a difference between light quantity at light-on and light quantity at light-out is regarded as received light quantity (returning amount). Then, this received light quantity is converted to a distance between the infrared thermometer 1 and the human skin.

Figure 19:
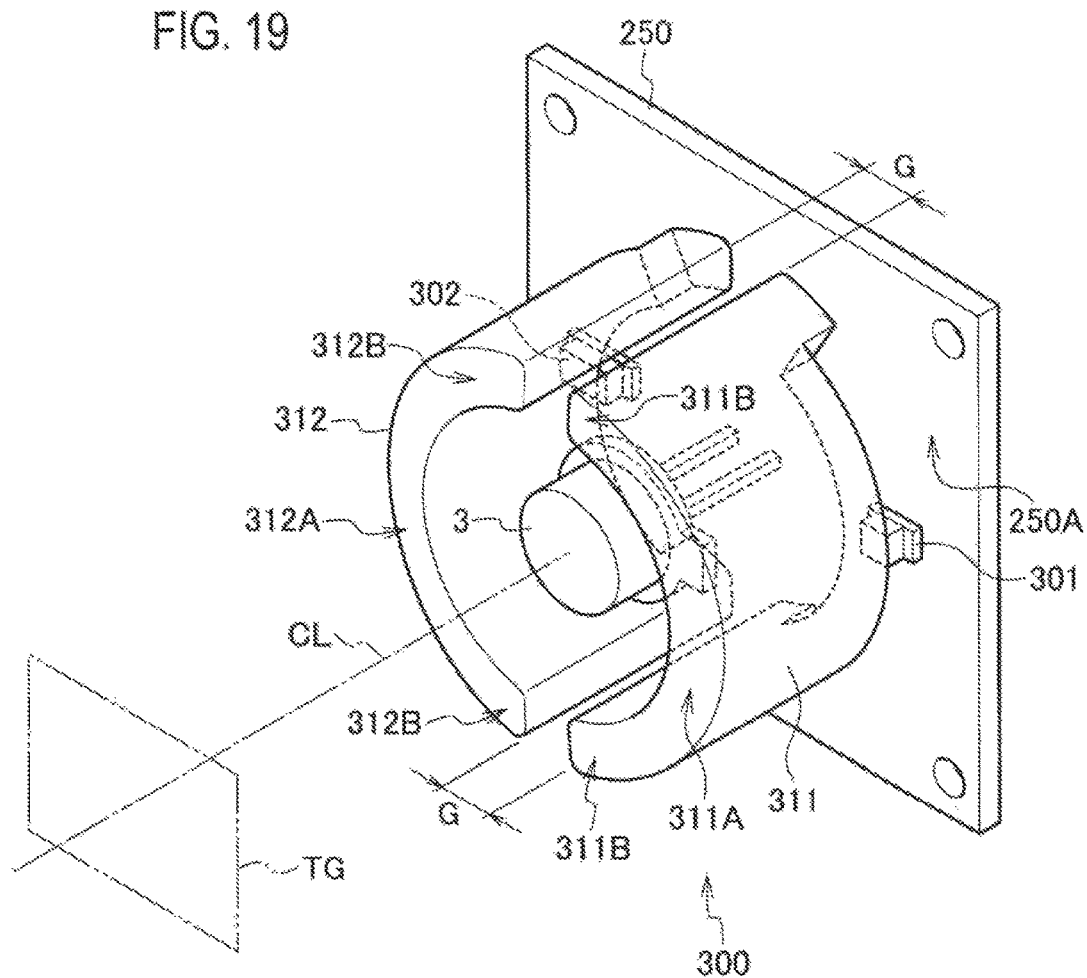
FIG. 19 is a perspective view illustrating the circuit board, on which the distance sensor and the infrared sensor of the infrared thermometer according to the second embodiment are mounted, and a target.
Figure 20:
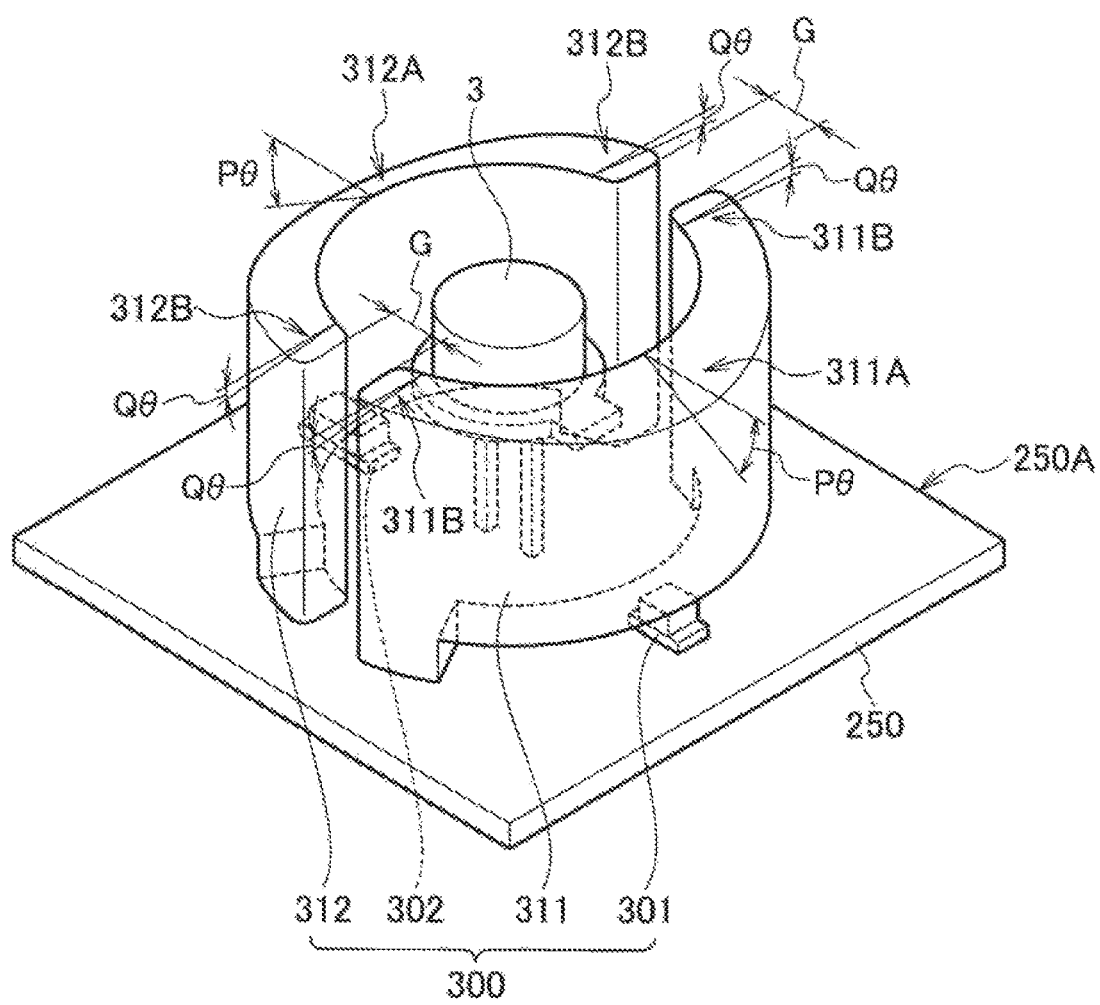
FIG. 20 is a perspective view illustrating the distance sensor of the infrared thermometer according to the second embodiment and the circuit board.

As illustrated in FIGS. 16 and 17, both the projector lens 311 and the light receiving lens 312 are composed of semi-circular arc-shaped lenses. As illustrated in FIGS. 19 and 20, the projector lens 311 and the light receiving lens 312 are fixed on the circuit board 250 so as to face each other at a distance G. Plastic lenses, for example, acrylic lenses are available for the projector lens 311 and the light receiving lens 312, preferably. The acrylic lens has a refractive index of 1.49, provided the refractive index of air is 1.0.

As illustrated in FIG. 17 which illustrates a cross-section indicated with a line A-A of FIG. 16, the projector lens 311 is provided, at the middle position, with a tip 311A which is inclined so as to lower toward the outside at an angle P$\theta$. Similarly, the light receiving lens 312 is provided, at the middle position, with a tip 312A which is inclined so as to lower toward the outside at an angle P$\theta$.

Figure 18:
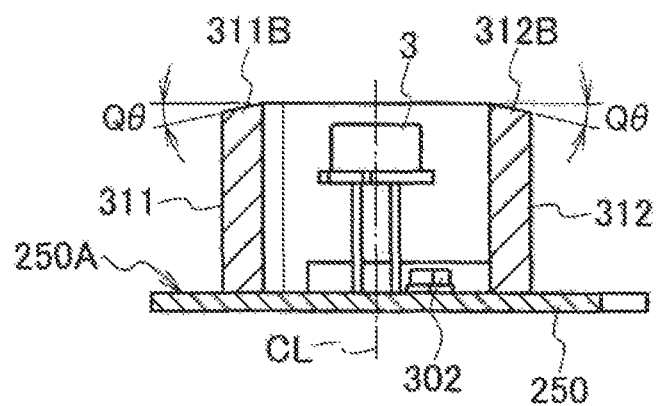
FIG. 18 is a cross sectional view taken along a line B-B of FIG. 16.

Additionally, as illustrated in FIG. 18 which illustrates a cross-section indicated with a line B-B of FIG. 16, the projector lens 311 is provided, at its left and right ends, with tips 311B each of which is inclined so as to lower toward the outside at an angle Q$\theta$. Similarly, the light receiving lens 312 is provided, at its left and right ends, with a tip 312B each of which is inclined so as to lower toward the outside at an angle Q$\theta$. The angle P$\theta$ is greater than the angle Q$\theta$.

As illustrated in FIG. 17, the light source 301 is arranged so as to face a rear end 311C of the tip 311A at the middle position (center position) of the projector lens 311. This rear end face 311C is formed with a first concave-lens portion 311D for receiving the light emitted from the light source 301. The light emitted from the light source 301 can be received by the first concave-lens portion 311D, then transmitted through the projector lens 311 and finally projected from the tip of the projector lens 311. The first concave-lens portion 311D is opposed to the light source 301.

As illustrated in FIG. 17, the light receiving sensor 302 is arranged so as to face a rear end 312C at the middle position (center position) of the light receiving lens 312. The rear end face 312C is formed with a second concave-lens portion 312D. The second concave-lens portion 312D allows the light receiving sensor 302 to receive the return light LR transmitted through the light receiving lens 312. The second concave-lens portion 312D is opposed to the light receiving sensor 302.

As illustrated in FIGS. 16 and 19, the projector lens 311 and the light receiving lens 312 are fixed to the circuit board 250 so as to concentrically surround around the center line CL as the center of the infrared sensor 3 while leaving a space.

Here, the configurations of the projector lens 311 and the light receiving lens 312 will be described in more detail.

As illustrated in FIG. 20, the tip 311A at the middle position of the projector lens 311 is slanted with a predetermined angle (the angle P$\theta$ illustrated in FIG. 17). This angle changes gradually as advancing from the tip 311A at the middle position up to the tips 311B of the left and right ends along the semicircular periphery. Consequently, at the tips 311B of the left and right ends of the projector lens 311, the angle is reduced to an angle Q$\theta$, as also illustrated in FIG. 18.

Similarly, the tip 312A at the middle position of the light receiving lens 312 is slanted with a predetermined angle (the angle P$\theta$ illustrated in FIG. 17). This angle changes gradually as advancing from the tip 312A at the middle position up to the tips 312B of the left and right ends along the semicircular periphery. Consequently, at the tips 312B of the left and right ends of the light receiving lens 312, the angle is reduced to an angle Q$\theta$, as illustrated in FIG. 18.

Thus, as the projector lens 311 is constructed so that its projection angle (emission angle) changes from the angle P$\theta$ to the angle Q$\theta$ along the semicircular profile successively, the light L transmitted through the projector lens 311 can focus at a position PP of FIG. 21 where the center axis CL intersects with the target TG.

Additionally, the light receiving lens 312 is also constructed so that its light receiving angle (incident angle) changes from the angle P$\theta$ to the angle Q$\theta$ along the semicircular profile successively. Thus, the light receiving lens 312 is adapted so that even if the return light LR from the target TG diffuses at the reflection on the position PP (skin) of FIG. 21 where the center axis CL intersects with the target TG, the light receiving lens 312 could allow an incidence of the diffused return light LR successfully.

In this way, the tip 311A of the projector lens 311 is shaped so that any light L transmitted through the projector lens 311 passes through the position PP where the central axis CL intersects with the target TG. Although the light L is projected from an area extending from the center position (middle position) 311A of the projector lens 311 up to the left and right tips 311B, the light L transmitted through the center position (middle position) 311A of the projector lens 311 passes through the position PP of the central axis L in the shortest run, while the distance up to the position PP gets longer as advancing to the right/left tips 311B of the projector lens 311.

Although the return light LR reflected by the target TG diffuses, the diffused return light LR is incident on the light receiving lens 312 in an area extending from the center tip 312A up to the tips 312B at the right/left ends and finally received by the light receiving sensor 302 through the second concave-lens portion 312D.

Thus, when allowing the light L emitted from the light source 301 to be reflected by the skin and then allowing the return light LR to be received by the light receiving sensor 302, the controller 150 can detect a change in the quantity of received light, as a change in distance with a high precision.

As illustrated in FIG. 21, it illustrates a situation where the light L from the light source 301 is reflected by the target TG, for example, the surface of a baby's skin and subsequently received, as the return light LR, by the light receiving sensor 302. As illustrated in FIG. 21, the light L from the light source 301 is transmitted through the projector lens 311. Subsequently, through a focal length FC, the transmitted light is converged and reflected on the surface of the baby's skin as a target surface, namely, the position PP where the center axis CL intersects with the target TG. After passing through the focal length FC, the reflected return light LR is transmitted through the light receiving lens 312 and received by the light receiving sensor 302.

Figure 22:
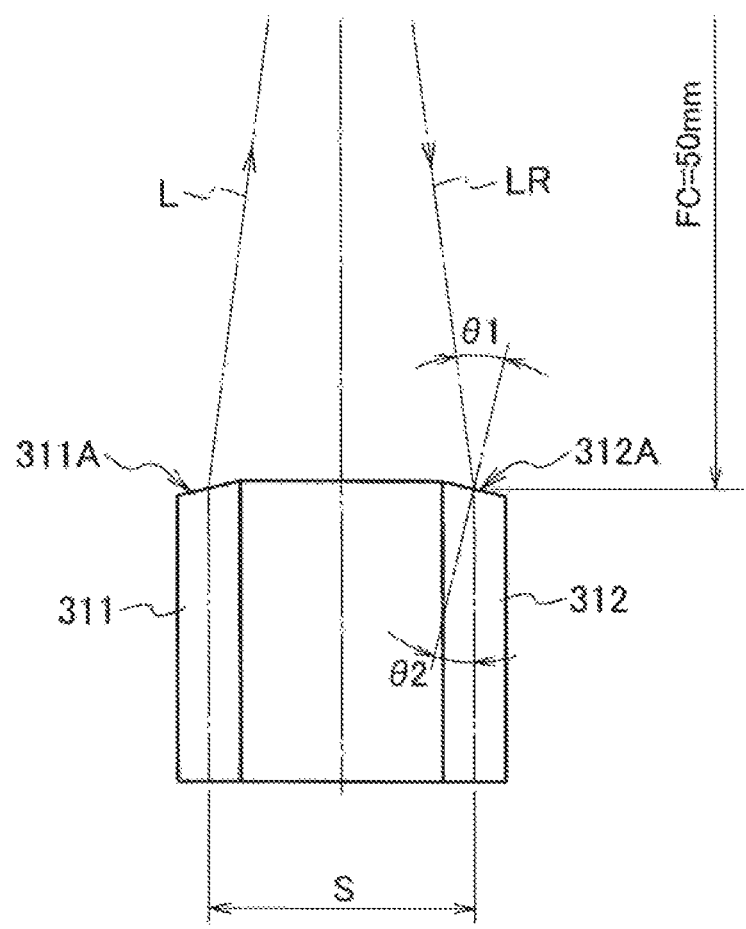
FIG. 22 is a diagram illustrating an example where the focal length at the tip of a projector lens and at the tip of a light receiving lens is 50 mm in the infrared thermometer according to the second embodiment.

FIG. 22 illustrates an example of the case that the focal length FC at the tip 311A of the middle position of the projector lens 311 and at the tip 312A of the middle position of the light receiving lens 312 is 50 mm. In this case, the refraction angle $\theta 1$ for the light L and the return light LR is, for example, 20.313°, while the incident angle $\theta 2$ at that time is 13.47°.

Figure 23:
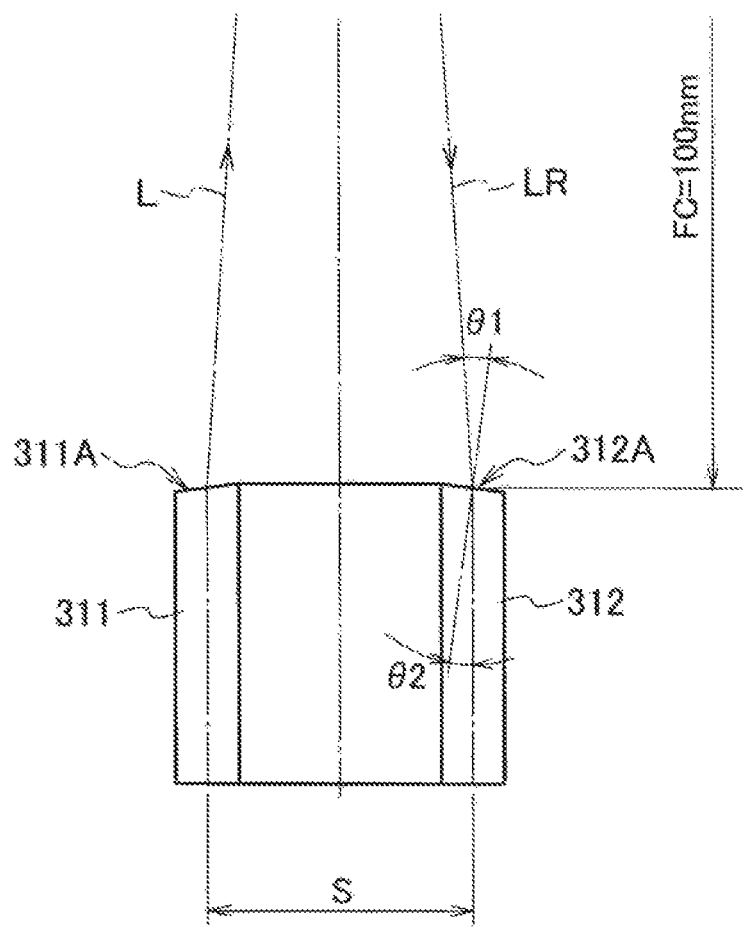
FIG. 23 is a diagram illustrating an example where the focal length at the tip of the projector lens and at the tip of the light receiving lens is 100 mm in the infrared thermometer according to the second embodiment.

Additionally, FIG. 23 illustrates an example of the case that the focal length FC at the tip 311A of the middle position of the projector lens 311 and at the tip 312A of the middle position of the light receiving lens 312 is 100 mm. In this case, the refraction angle θ1 for the light L and the return light LR is, for example, 10.344°, while the incident angle θ2 at that time is 6.910.

In FIGS. 22 and 23, there are schematically illustrated the refraction angle θ1 of the projector lens 311 and the light receiving lens 312, and respective positions of the light L and the return light LR appearing on the target TG at that time.

In the examples of FIGS. 22 and 23, the focal lengths FC of the projector lens 311 and the light receiving lens 312 are, for example, 50 mm and 100 mm, respectively. Without being limited to these examples, however, the focal length FC of the projector lens 311 and the light receiving lens 312 may be set in the range from 1 mm at minimum to 200 mm at maximum, preferably.

The focal length FC less than 1 mm is not desirable because the infrared thermometer 1 is brought into contact with the skin. Further, if the focal length FC is greater than 200 mm, it becomes difficult to measure the body temperature since the quantity of infrared from the skin gets too smaller. That is, although the maximum of the measurable predetermined focal length FC illustrated in FIG. 21 is proportional to the outside diameters (radius) of the projector lens 311 and the light receiving lens 312, the focal length FC can be set to 200 mm at maximum in consideration of the size of the distance sensor 300 installable in the infrared thermometer 1 and the light quantity that can be secured.

The measurement is based on the premise that the focal length FC is proportional to the light quantity of the returned light LR. However, if the focal length FC is long, the light is diffused and attenuated to cause the light quantity of the return light LR to be reduced. Thus, under the large focal length FC, the attenuation of the light quantity of the return light LR becomes too large, so that the difference between the return light LR and the external light gets smaller. For this reason, with use of the projector lens 311 and the light receiving lens 312 disposed opposite with each other on the circuit board 250, this embodiment adopts the structure where the light L projected from the projector lens 311 is reflected by the target TG and thereafter, the return light LR from the position PP of the target TG is received by the light receiving sensor 302 through the light receiving lens 312.

Since there is a restriction in the capacity of the battery 221 installable in the compact infrared thermometer 1, the structure of the distance sensor 300 is considered so as to perform a contactless measurement of the body temperature with power saving and high accuracy. The distance sensor 300 of the compact infrared thermometer 1 can ensure a sufficient brightness against the external light, provided that the electrical power can be secured sufficiently.

Next, the operation of the infrared thermometer 1 will be described.

First, when turning on the power switch 13 of the infrared thermometer 1 to supply an operating voltage from the 3 volts battery 221 arranged in the battery housing part 15 to the infrared thermometer 1, the infrared sensor 3 and the distance sensor 300 of the infrared thermometer 1 start their operation by a command of the controller 150.

Next, in measuring the temperature of a human body (e.g. forehead skin), a measurer pinches the concave portion 1A of the mortar-shaped infrared thermometer 1 by fingers etc. in order to measure the distance between the human skin and the infrared thermometer 1 and moves the mortar-shaped portion 1C (the apex portion 1B) of the main unit 1R of the infrared thermometer 1 closer to the human body (e.g. forehead skin). As illustrated in FIG. 21, the light L from the light source 301 is transmitted through the projector lens 311 and projected toward the human body (e.g. forehead skin) as the target TG.

Then, as illustrated in FIG. 21, when the distance sensor 300 approaches the target TG so that the light L from the light source 301 is focused on the target TG through the projector lens 311, this light L is reflected by the target TG and subsequently received, as the return light LR, by the light receiving sensor 302 through the light receiving lens 312.

As illustrated in FIG. 21, when the light L from the light source 301 is focused on the target TG at the predetermined focal length FC (e.g. 50 mm) through the projector lens 311, the quantity of light received by the light receiving sensor 302 becomes maximum in comparison with a case that the distance between the distance sensor 300 of the infrared thermometer 1 and the target TG is not the predetermined focal length FC (e.g. 50 mm). Thus, in the controller 150, the signal-level value of the light receiving signal RS transmitted from the light receiving sensor 302 to the controller 150 is maximized. In connection, the case that it is not the predetermined focal length FC means a situation where the distance between the distance sensor 300 of the infrared thermometer 1 and the target TG is not e.g. 50 mm, that is, the infrared thermometer 1 is further away from the skin than 50 mm or closer to the skin than 50 mm.

On detection of the signal-level value of the light receiving signal RS, the controller 150 allows the liquid crystal display unit 11 to display that it is possible to measure the body temperature and notifies a measurer. That is, when the infrared thermometer 1 is located in an appropriate measuring position with respect to the human skin, the measurer is informed of "body-temperature measuring state". Then, the controller 150 calculates the body temperature of the human body based on the quantity of infrared from the infrared sensor 3, which is obtained by a body-temperature measurement signal TK from the infrared sensor 3, at the time when the signal-level value of the light receiving signal RS transmitted from the light receiving sensor 302 to the controller 150 is maximized. In this way, it is possible to acquire a measured value of the body temperature.

Note that the measurer is ignorant of whether or not the body temperature has been measured correctly. Therefore, if the body-temperature measurement has been successful fairly, the controller 150 actuates notification means (e.g. the buzzer 180) for its sounding and allows the liquid crystal display unit 11 to display the fact that the body-temperature measurement was successful. Accordingly, the measurer can reliably recognize that the body-temperature measurement was successful, in the manner of sight and hearing.

In this way, by using the distance sensor 300, the infrared thermometer 1 can measure the distance up to the human body as a subject correctly and thus detect the body temperature contactlessly while separating the infrared sensor 3 from the human body at an optimum distance.

Incidentally, when the temperature measured with use of the infrared sensor 3 is more than 28° C., this temperature can be regarded as the body temperature of the measuring object portion in the human body. However, if the temperature is less than 28° C., the controller 150 ignores the temperature on the assumption that the infrared thermometer may touch any object (e.g. clothes, hair) other than the human body or the infrared thermometer may be placed on a desk.

Although the infrared sensor 3 is responsive to conductive materials, it does not react to such as a desk made from wood or plastic. Furthermore, the infrared sensor 3 reacts to such as a desk made from metal or the like. Nevertheless, when the room temperature is not high, the temperature at this time is ignored since it does not become as high as the body temperature.

As described above, according to the second embodiment, the infrared sensor 3 of the infrared thermometer 1 is capable of measuring the body temperature while avoiding the contact with the human skin, in other words, contactlessly. For this reason, as the infrared thermometer 1 does not touch the human skin as a subject, such as a baby, there is no transfer in temperature during the contactless body-temperature measurement, thereby allowing the body temperature to be measured more precisely.

In the second embodiment, the infrared sensor 3 of the infrared thermometer 1 measures the body temperature contactlessly with the human skin and displays the body temperature on the liquid crystal display unit 11. Therefore, it is very effective in measuring the body temperature of a baby or an infant who is apt to be constantly on the move when measuring the body temperature, for example, a subject turning its back and refusing the measurement. That is, as an infant or baby etc. moves its face reflexively as soon as an object touches, it is very effective that the infrared thermometer 1 according to the second embodiment can measure the body temperature contactlessly and it is possible to measure the body temperature of the infant etc. without failure, reliably and simply.

Additionally, the infrared thermometer 1 has also a function of converting the temperature of a forehead surface to the temperature of an underarm for display. Then, it is necessary to measure the temperature of the forehead surface at a specific location, such as a forehead's center. This is because there is a need of measuring the temperature derived from an artery in the vicinity of this region.

Next, preferred examples in the shape of the distance sensor 300 of the infrared thermometer 1 according to the second embodiment will be described with reference to FIGS. 24 to 27.

Figure 24:
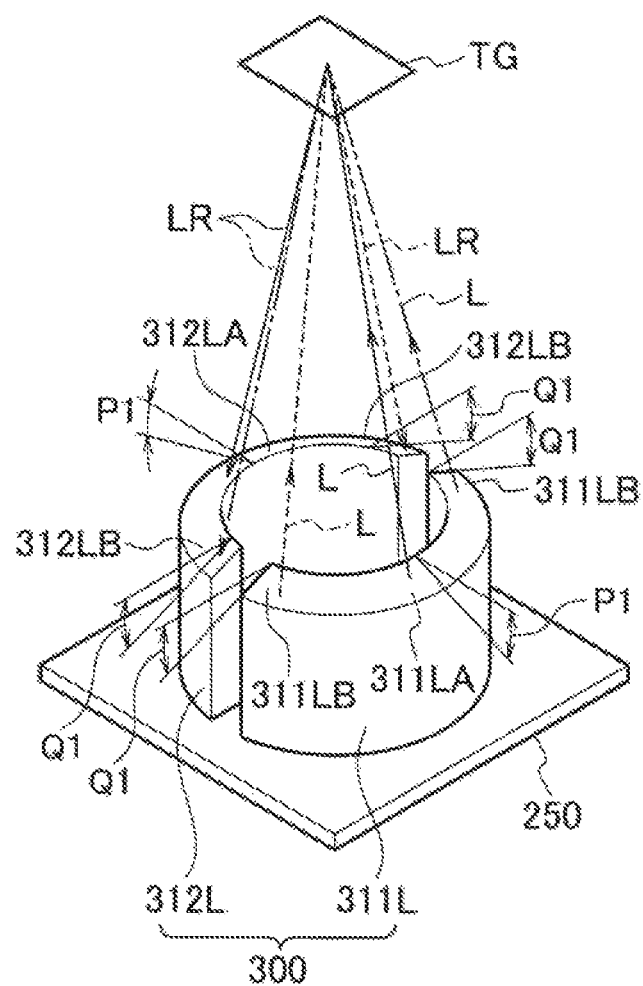
FIG. 24 is a perspective view illustrating a situation where the profiles of respective tips of the projector lens and the light receiving lens become constant in the infrared thermometer according to the second embodiment.

FIG. 24 illustrates a preferred example in the shape of the distance sensor 300. In the distance sensor 300, the profiles of the tips of a projector lens 311L and a light receiving lens 312L are inclined at constant angles from their center positions up to the left and right positions so as to allow their focal lengths to be fixed to 50 mm, respectively. In FIG. 24, there is illustrated an example of optical paths of the light L from the projector lens 311L and the return light LR reflected by the target TG at the position of 50 mm.

The projector lens 311L and the light receiving lens 312L have respective top-surface profiles (tip shapes) allowing fixed lengths of 50 mm in the focal length to be measured respectively. The tip of the projector lens 311L and the tip of the light receiving lens 312L are inclined at the same angle, continuously from respective center positions up to their left and right positions. In the projector lens 311L and the light receiving lens 312L, accordingly, their tip positions 311LA, 312LA at the center positions are inclined so as to lower toward the outside at an angle P1. In the projector lens 311L and the light receiving lens 312L, additionally, their tip positions 311LA, 312LA at the left and right ends are inclined so as to lower toward the outside at an angle Q1. The angle P1 is set equal to the angle Q1 (i.e. P1=Q1).

In this case, despite that the projector lens 311L and the light receiving lens 312L have their focal lengths fixed at 50 mm respectively, there exists a return light even outside of 50 mm due to diffusion or diffused reflection of light. Nevertheless, it is possible to recognize the distance of around 50 mm by the intensity of light.

Figure 25:
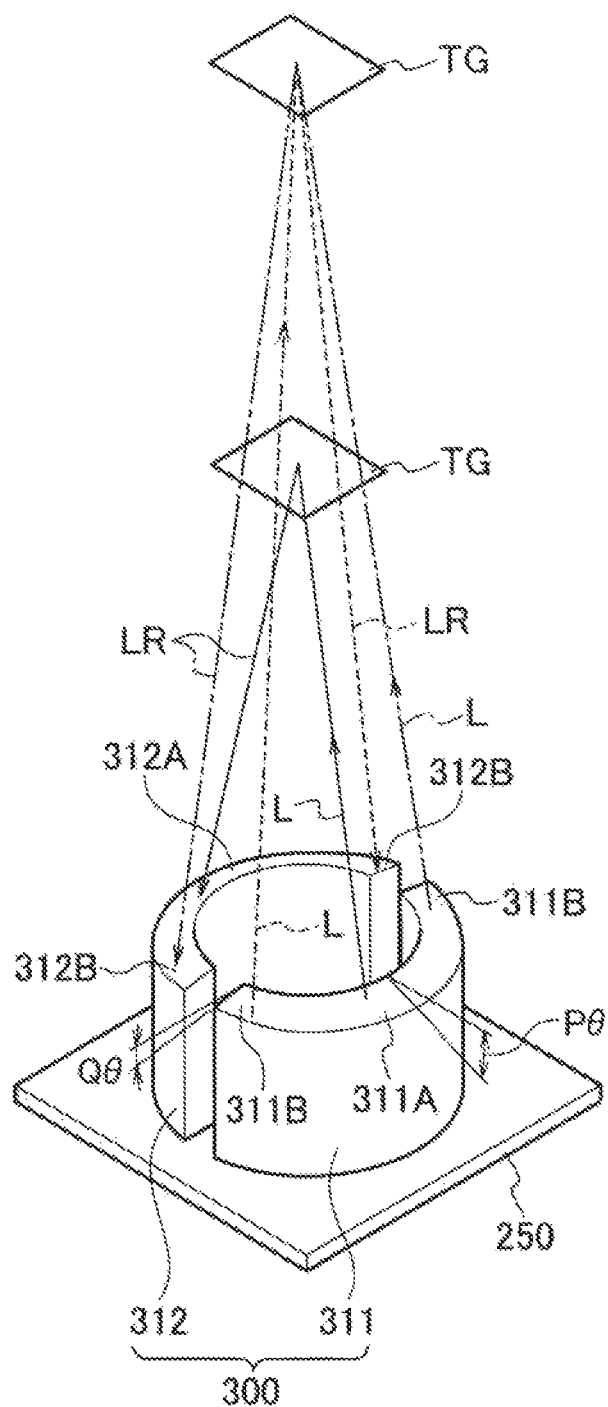
FIG. 25 is a perspective view illustrating a situation where the profiles of respective tips of the projector lens and the light receiving lens vary continuously and smoothly.

Next, FIG. 25 illustrates another preferred example in the shape of the distance sensor 300. In the distance sensor 300, the profiles of the tips of the projector lens 311 and the light receiving lens 312 are continuously-changed smoothly so that their respective focal lengths (focuses) become 50 mm-100 mm. In FIG. 25, there is illustrated an example of optical paths of the light L from the projector lens 311 and the return light LR reflected by the target TG at the positions of 50 mm and 100 mm.

The projector lens 311 and the light receiving lens 312 have respective top-surface profiles (tip shapes) allowing respective focal lengths to be measured in the range from 50 mm to 100 mm. The tip of the projector lens 311 and the tip of the light receiving lens 312 are inclined so as to continuously change from respective tips 311A, 312A at the center positions up to their left and right positions 311B, 312B smoothly. In the projector lens 311 and the light receiving lens 312, accordingly, their tips 311A, 312A at the center positions are inclined so as to lower toward the outside at an angle Pθ. In the projector lens 311 and the light receiving lens 312, additionally, their tips 311B, 312B at the left and right ends are inclined so as to lower toward the outside at an angle Qθ. The angle Pθ is set greater than the angle Qθ (i.e. Pθ>Qθ).

In this way, the profiles of the tips of the projector lens 311 and the light receiving lens 312 are continuously and smoothly changed from the tips at the center position up to the left and right end positions so as to allow their focal lengths to be measured in the range from 50 mm to 100 mm, respectively. In the relationship between the angle P1 illustrated in FIG. 24 and the angle Pθ illustrated in FIG. 25, there is established an equality of angles P1=Pθ. In the relationship between the angle Q1 illustrated in FIG. 24 and the angle Qθ illustrated in FIG. 25, there is established an inequality of angles Q1>Qθ.

Then, in the tip profiles of the projector lens 311 and the light receiving lens 312, the angle Pθ is set so that respective focal lengths become 50 mm, while the angle Qθ is set so that respective focal lengths become 100 mm. Between the angle Pθ and the angle Qθ, the angle changes smoothly and continuously. As for the setting range of this focal length, assuming that the minimum focal length (50 mm) corresponds to a single-point position at the center in the profiles of the tips of the projector lens 311 and the light receiving lens 312, the angle is distributed toward the left and right positions in the tip profiles of the projector lens 311 and the light receiving lens 312 so that the focal length exceeds 50 mm and reaches 100 mm. This is because of the following reasons. That is, if the focal length is long, then a reach distance is prolonged to attenuate the light L. Therefore, by allowing the light L projected from the projector lens 311 to be reflected by the target TG and returning the return light LR to the tip side of the light receiving lens 312 from two directions, it is intended to ensure the quantity of received light. Incidentally, when the light L is sufficiently strong, there is no need of returning the return light LR toward the tip of the light receiving lens 312 from two directions.

Figure 26:
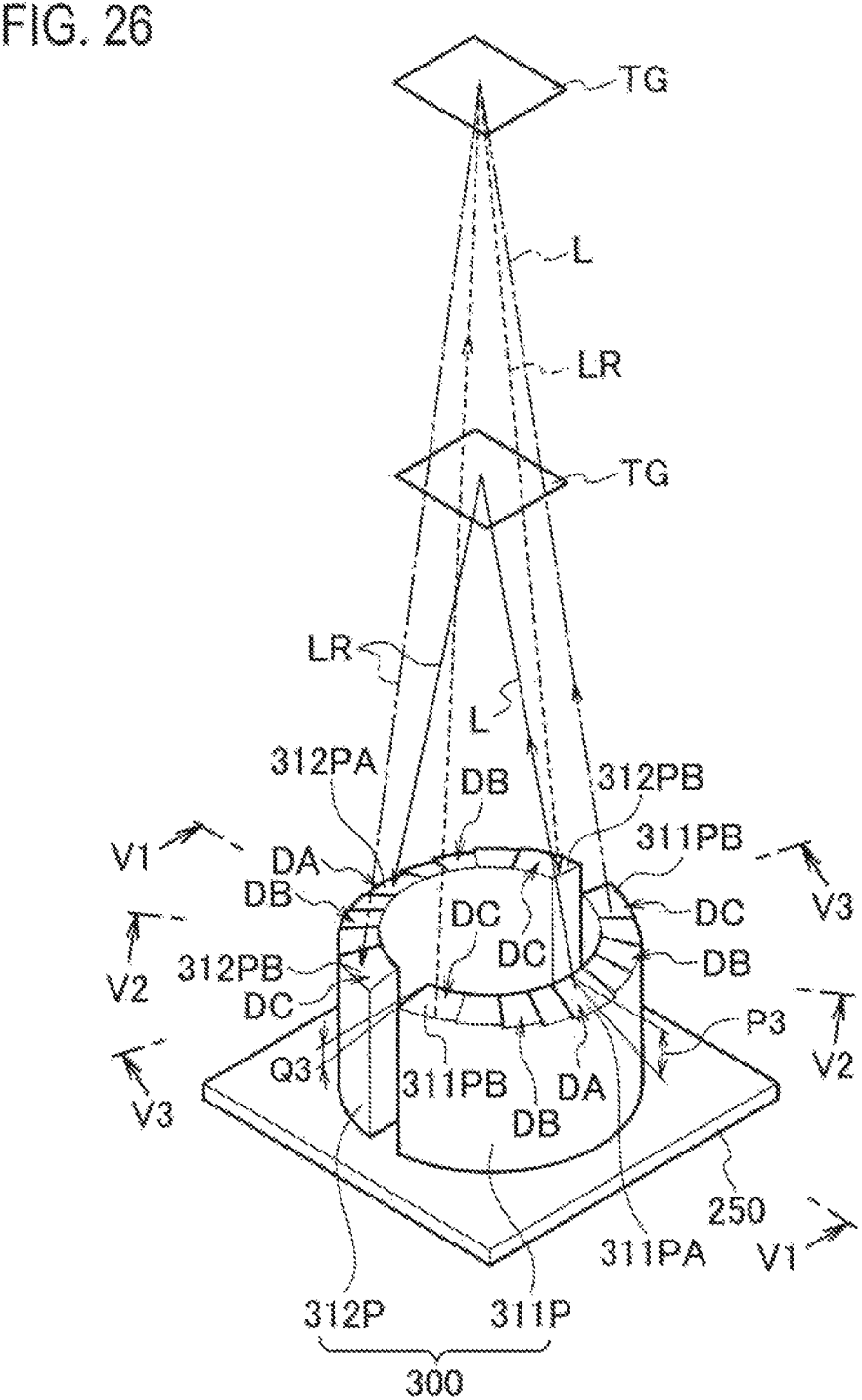
FIG. 26 is a perspective view illustrating a situation where the profiles of respective tips of the projector lens and the light receiving lens vary in a stepwise shape.

FIG. 26 illustrates yet another preferred example in the shape of the distance sensor 300. In the distance sensor 300, the profiles of the tips of the projector lens 311P and the light receiving lens 312P are changed stepwise so that their respective focal lengths (focuses) become 50 mm-100 mm. In FIG. 26, there is illustrated an example of optical paths of the light L from the projector lens 311P and the return light LR reflected by the target TG at the positions of 50 mm and 100 mm.

The projector lens 311P and the light receiving lens 312P have respective top-surface profiles (tip profiles) allowing respective focal lengths to be measured within the range from 50 mm to 100 mm. The tip of the projector lens 311P and the tip of the light receiving lens 312P are inclined so as to change from respective center portions up to their left and right positions in a stepwise shape. In the projector lens 311P and the light receiving lens 312P, accordingly, their tip positions 311PA, 312PA at the center positions are inclined so as to lower toward the outside at an angle P3. In the projector lens 311P and the light receiving lens 312P, additionally, their tip positions 311PB, 312PB at the left and right ends are inclined so as to lower toward the outside at an angle Q3.

The relationship between the angle P3 and angle Q3 is set to P3>Q3. Thus, the tip profiles of the projector lens 311P and the light receiving lens 312P vary in a stepwise shape by providing a plurality of steps from the tips at the center positions up to the tips in the left and right positions so as to allow respective focal lengths to be measured within the range from 50 mm to 100 mm. Note that, in the relationship among the angle P1 illustrated in FIG. 24, the angle P$\theta$ illustrated in FIG. 25, and the angle P3 illustrated in FIG. 26, there is established an equality of angles P1=P$\theta$=P3. Additionally, the relationship between the angle Q$\theta$ illustrated in FIG. 25 and the angle Q3 illustrated in FIG. 26 is represented by an equality of angles Q$\theta$=Q3.

In this case, the tip profiles of the projector lens 311P and the light receiving lens 312P illustrated in FIG. 26 vary in a stepwise shape so that respective focal lengths change from 50 mm at the angle P3 toward 100 mm at the angle Q3, respectively. As for the setting range of this focal length, assuming that the minimum focal length (50 mm) corresponds to a single-point position at each center in the tip profiles of the projector lens 311P and the light receiving lens 312P, the angle is distributed toward the left and right positions in the tip profiles of the projector lens 311P and the light receiving lens 312P.

Figure 27A:
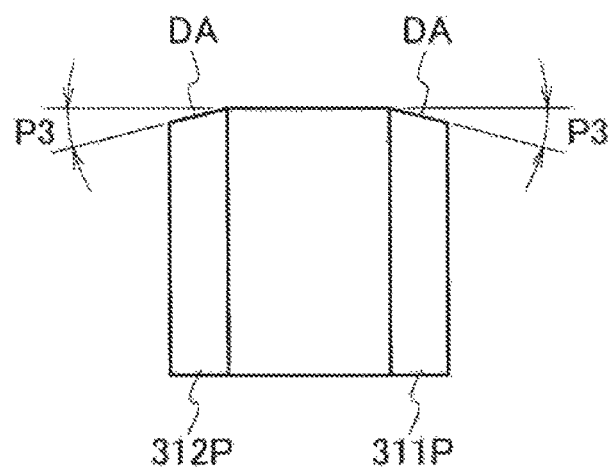
FIG. 27A is a cross sectional view taken along a line V1-V1 of the profiles of respective tips of the projector lens and the light receiving lens of FIG. 26, FIG. 27B a cross sectional view taken along a line V2-V2 of the same profiles.
Figure 27B:
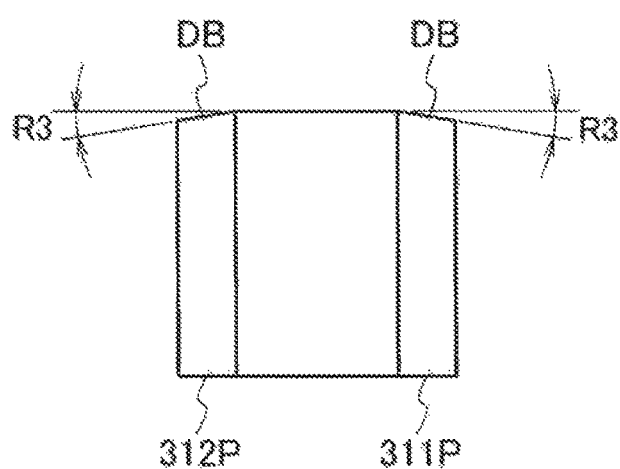
FIG. 27C is a cross sectional view taken along a line V3-V3 of the same profiles.
Figure 27C:
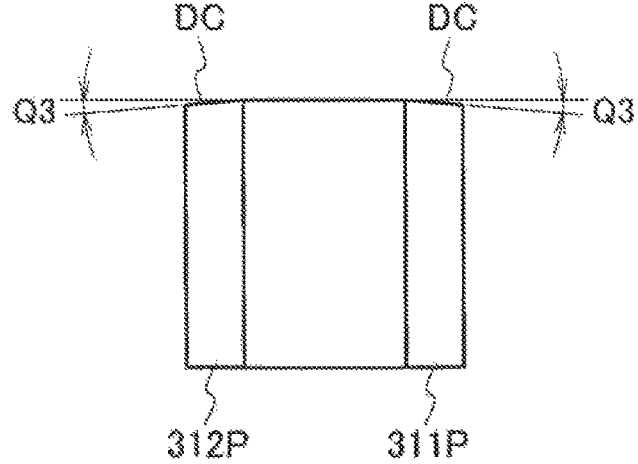

FIG. 27A illustrates respective inclinations of center step parts DA of the tip, FIG. 27B illustrated respective inclinations of step parts DB outside the center step parts DA of the tips, and FIG. 27C illustrates respective inclinations of step parts DC on either side of the tips. The relationship among the angle P3 of the center step parts DA, the angle R3 of the step parts DB and the angle Q3 of the left and right step parts DC of the tips is represented by an inequality of angles P3>R3>Q3. The reason why such a structure is adopted is because of the following reasons. That is, if the focal length is long, then a reach distance is prolonged to attenuate the light L. Therefore, by allowing the light L projected from the projector lens 311P to be reflected by the target TG and returning the return light LR to the tip of the light receiving lens 312P from two directions, it is intended to ensure the quantity of received light.

In the stepwise tip profiles of the projector lens 311P and the light receiving lens 312P illustrated in FIG. 26, they includes steps for every e.g. 10 mm in focal length and are adapted so as to enable the received light quantity of the return light LR to be ensured since the area of these steps is gradually broadened as advancing from the center position toward the positions of the left and right ends. The received light quantity of the return light LR can be controlled by designing of the area of the step parts. However, if the received light quantity of the return light LR is sufficiently strong, it is not necessary to return the return light LR to the tip of the light receiving lens 312P from two directions and therefore, there is no need of designing the area of the step parts.

As the distance sensor 300 illustrated in FIGS. 25 and 26 has a single light receiving sensor 302 (see FIG. 16) on the side of the light receiving lens, the change in distance must be regarded as a change in light quantity. Therefore, it becomes important to control the light quantity of the return light LR by the design of the tip profiles of the projector lens and the light receiving lens.

For the distance sensor 300, additionally, there may be adopted a combination structure composed of the projector lens and the light receiving lens illustrated in FIGS. 24 to 26. That is, although the arrangement illustrated in FIG. 24 is adapted so as to recognize around a design value by diffusion or irregular reflection of light, its recognition range is narrow. Thus, by combining the projector lens and the light receiving lens illustrated in FIGS. 24 to 26, it is possible to obtain a projector lens and a light receiving lens each having a certain range of focal length.

The infrared thermometer 1 of the second embodiment is capable of measuring the body temperature without contact to the human body and includes the main unit 1R incorporating the infrared sensor 3, the distance sensor 300 for detecting the distance between the main unit 1R and the human body when the main unit 1R approaches the human body and the controller 150 for calculating the body temperature of the human body based on the quantity of infrared from the infrared sensor 3 when it is detected through the distance sensor 300 that the distance between the main unit 1R and the human body becomes equal to a predetermined distance (the focal lengths FC of the projector lens 311 and the light receiving lens 312). The distance sensor 300 includes the light source 301 that emits the light L, the projector lens 311 for projecting the light L of the light source 301 toward the human body, the light receiving sensor 302 and the light receiving lens 312 that allows the light receiving sensor 302 to receive the return light LR of the projected light L, which is obtained as a result of being reflected by the human body, when the main unit 1R is located at the predetermined distance (FC).

Consequently, when the main unit is located at the predetermined distance, the infrared thermometer 1 allows the light receiving sensor to receive the return light of the projected light, which is obtained as a result of being reflected by the human body and calculates the body temperature of the human body based on the quantity of infrared from the infrared sensor 3 at the predetermined distance. Thus, the infrared thermometer, despite its simple structure, does not touch the skin of the human body as the subject (e.g. baby). Therefore, there is no transfer of the body temperature during the measurement of the body temperature in a non-contact state, so that it is possible to measure the body temperature precisely.

In the infrared thermometer 1, both the projector lens 311 and the light receiving lens 312 are composed of semi-circular arc-shaped lenses in common. Thus, by adopting semi-circular arc-shaped lenses for the projector lens 311 and the light receiving lens 312 together, it is possible to arrange the infrared sensor 3 between the projector lens and the light receiving lens. Therefore, the layout of the infrared sensor 3 in the main unit 1R is easy and accordingly, miniaturization of the main unit 1R can be carried out.

The infrared thermometer 1 includes the circuit board 250 on which the projector lens 311, the light receiving lens 312 and the infrared sensor 3 are mounted. In the infrared thermometer 1, the infrared sensor 3 is arranged between the projector lens 311 and the light receiving lens 312, and the projector lens 311 and the light receiving lens 312 are arranged at symmetrical positions with respect to the center axis CL passing through the infrared sensor 3, as a center. As a result, without being obstructed by the projector lens 311 and the light receiving lens 312, the infrared sensor 3 can receive infrared radiation from the human body through an interval between the projector lens 311 and the light receiving lens 312.

In the infrared thermometer 1, the circuit board 250 mounting the projector lens 311, the light receiving lens 312 and the infrared sensor 3 is disposed in the apex portion 1B of the main unit 1R. Thus, it is possible to direct the distance sensor 300 and the infrared sensor 3 of the circuit board 250 to the measuring object portion of the human body, for example, a skin of a baby's forehead etc. easily and also possible to measure the distance between the apex portion 241 of the inner structure 240 and the skin of the forehead etc. and the quantity of infrared from the skin of the forehead etc. directly without being obstructed by the other elements. The body temperature can be measured by moving the apex portion of the main unit closer to the human body.

To use the relationship between the received light quantity and the distance contributes to a removal of individual differences in manufacturing the infrared thermometers, allowing the accuracy of body-temperature measurement by the infrared thermometer to be ensured.

Although one example has been illustrated hereinbefore, it is needless to say that the present application may be modified in any way.

As for the notification means, it is not limited to the liquid crystal display 11 or the buzzer 180, but may be an organic EL display unit, a speaker or the like.

What is claimed is:

1. An infrared thermometer capable of measuring a body temperature in no contact with a human body, comprising:
    a main unit;
    an infrared sensor accommodated in the main unit;
    a distance sensor configured to detect a distance between the main unit and the human body when the main unit approaches the human body; and
    a controller configured to calculate the body temperature of the human body based on quantity of infrared from the infrared sensor when the distance sensor detects that the distance between the main unit and the human body is within a predetermined distance, wherein
    the distance sensor comprises
        a light source for emitting light;
        a projector lens for projecting the emitted light from the light source toward the human body;
        a light receiving sensor; and
        a light receiving lens that allows the light receiving sensor to receive returned light, which is obtained as a result of the emitted light being reflected by the human body, when the distance between the main unit and the human body is within the predetermined distance, wherein
            the projector lens and the light receiving lens have a same semi-circular arc-shape, and at least partially and concentrically surround the infrared sensor.

2. The infrared thermometer of claim 1, further comprising
    a circuit board on which the projector lens, the light receiving lens, and the infrared sensor are mounted, wherein
    the infrared sensor is arranged between the projector lens and the light receiving lens, while the projector lens and the light receiving lens are arranged at symmetrical positions with respect to a center axis passing through the infrared sensor, as a center.

3. The infrared thermometer of claim 2, wherein
    the circuit board, which mounts the infrared sensor, the light receiving lens, and the projector lens thereon, is arranged in an apex portion of the main unit.

4. The infrared thermometer of claim 1, wherein
    a level of inclination of profile of each of a tip of the projector lens and a tip of the light receiving lens is a constant angle.

5. The infrared thermometer of claim 1, wherein
    a level of inclination of profile of each of a tip of the projector lens and a tip of the light receiving lens is continuously changed.

6. The infrared thermometer of claim 1, wherein
    a level of inclination of profile of each of a tip of the projector lens and a tip of the light receiving lens is changed stepwise.

* * * * *